United States Patent
Koyama et al.

(10) Patent No.: US 7,914,793 B2
(45) Date of Patent: Mar. 29, 2011

(54) METHOD FOR PRODUCING AN ANTIGENIC SUBSTANCE AND ANTIBODY

(76) Inventors: Shozo Koyama, Nagano (JP); Satoshi Tanaka, Nagano (JP)

( * ) Notice: Subject to any disclaimer, the term of this patent is extended or adjusted under 35 U.S.C. 154(b) by 579 days.

(21) Appl. No.: 10/786,369

(22) Filed: Feb. 26, 2004

(65) Prior Publication Data

US 2004/0230067 A1  Nov. 18, 2004

Related U.S. Application Data

(63) Continuation of application No. 09/881,664, filed on Jun. 18, 2001, now abandoned, which is a continuation of application No. 09/355,642, filed as application No. PCT/JP98/00351 on Jan. 28, 1998, now abandoned.

(30) Foreign Application Priority Data

Jan. 29, 1997 (JP) .................................... 9-028295

(51) Int. Cl.
 *A61K 39/00* (2006.01)
 *A61K 47/06* (2006.01)
 *G01N 33/531* (2006.01)
(52) U.S. Cl. .................. 424/184.1; 424/9.1; 424/277.1; 436/128
(58) Field of Classification Search .................. 435/326, 435/965, 961; 436/544, 547; 530/806; 568/306
 See application file for complete search history.

(56) References Cited

U.S. PATENT DOCUMENTS

| | | | |
|---|---|---|---|
| 4,081,458 A | 3/1978 | Flaugh | 260/335 |
| 4,147,672 A | 4/1979 | Schulte-Elte et al. | 252/522 |
| 4,264,467 A | 4/1981 | Schulte-Elte et al. | 252/174.11 |
| 4,289,659 A | 9/1981 | Schulte-Elte et al. | 252/522 R |
| 4,720,386 A * | 1/1988 | McCollester | 424/277.1 |
| 5,030,621 A * | 7/1991 | Bystryn | 424/277.1 |
| 5,169,993 A | 12/1992 | Briner | 568/807 |
| 5,194,384 A * | 3/1993 | Bystryn | 424/277.1 |
| 5,200,535 A | 4/1993 | Briner | 549/546 |
| 5,635,188 A * | 6/1997 | Bystryn | 424/277.1 |
| 6,338,853 B1 * | 1/2002 | Bystryn | 424/277.1 |
| 6,346,551 B1 * | 2/2002 | Koyoma et al. | 514/690 |
| 6,710,090 B2 * | 3/2004 | Koyama et al. | 514/690 |

FOREIGN PATENT DOCUMENTS

| | | |
|---|---|---|
| CH | 603 071 A | 8/1978 |
| JP | 50-105841 A | 8/1975 |
| JP | 51-105038 A | 9/1976 |
| JP | 4-316531 A | 11/1992 |
| JP | 9-221421 A | 8/1997 |
| WO | 96/07403 | 3/1996 |
| WO | 97/01633 | 1/1997 |

OTHER PUBLICATIONS

Koyama, S. et al.; "Apoptosis-like (possible quantum thermodynamic) cell death induced by Yoshixol and wood oil of *Chamaecyparis obstusa* (Kiso-Hinoki) on HeLa cell."; vol. 28, No. 5, (May 1997), pp. 805-811.
Koyama, S. et al.; "A new substance (Yoshixol) with an interesting antibiotic mechanism from wood oil of Japanese traditional tree (Kiso-Hinoki), *Chamaecyparis obtusa*."; vol. 28, No. 5, (May 1997).
International Search Report; PCT/JP98/00351; (Apr. 14, 1998).

* cited by examiner

*Primary Examiner* — Shafiqul Haq
(74) *Attorney, Agent, or Firm* — Kubovcik & Kubovcik

(57) ABSTRACT

This invention provides antigen substance inductors which produce highly selective and/or specific vaccine precursor, vaccine, antibody (including idiotype antibody), neutralizing antibody, antitoxin.
This invention is to produce and/or manufacture highly selective and/or specific vaccine precursor, vaccine, antibody (including idiotype antibody), neutralizing antibody, antitoxin by quantum thermodynamic and chemical control of molecular functions and morphogenesis, inducing non-functional complex macromolecules which form organism and/or non-organism and which become to be substance with fundamental structure more closed to an induction of the functions, utilizing the fundamental structure of molecule which is indicated in Formula 3-a as a representative molecule. Moreover, by those produced substances, this invention is to produce and/or manufacture antimicrobial agent, antiviral agent, neutralizing antibody, antitoxin, antitumor agent, anti-protozoa agent (malaria, spirochaeta et. al), molecular discriminating agent, antibody as labeled compounds, histocompatible accelerator on tissues or organs, immuno-response accelerator or immuno-response controller, complement chain reaction accelerator.

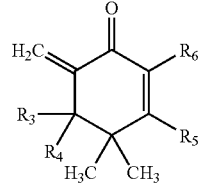

Formula 3-a

1 Claim, 14 Drawing Sheets

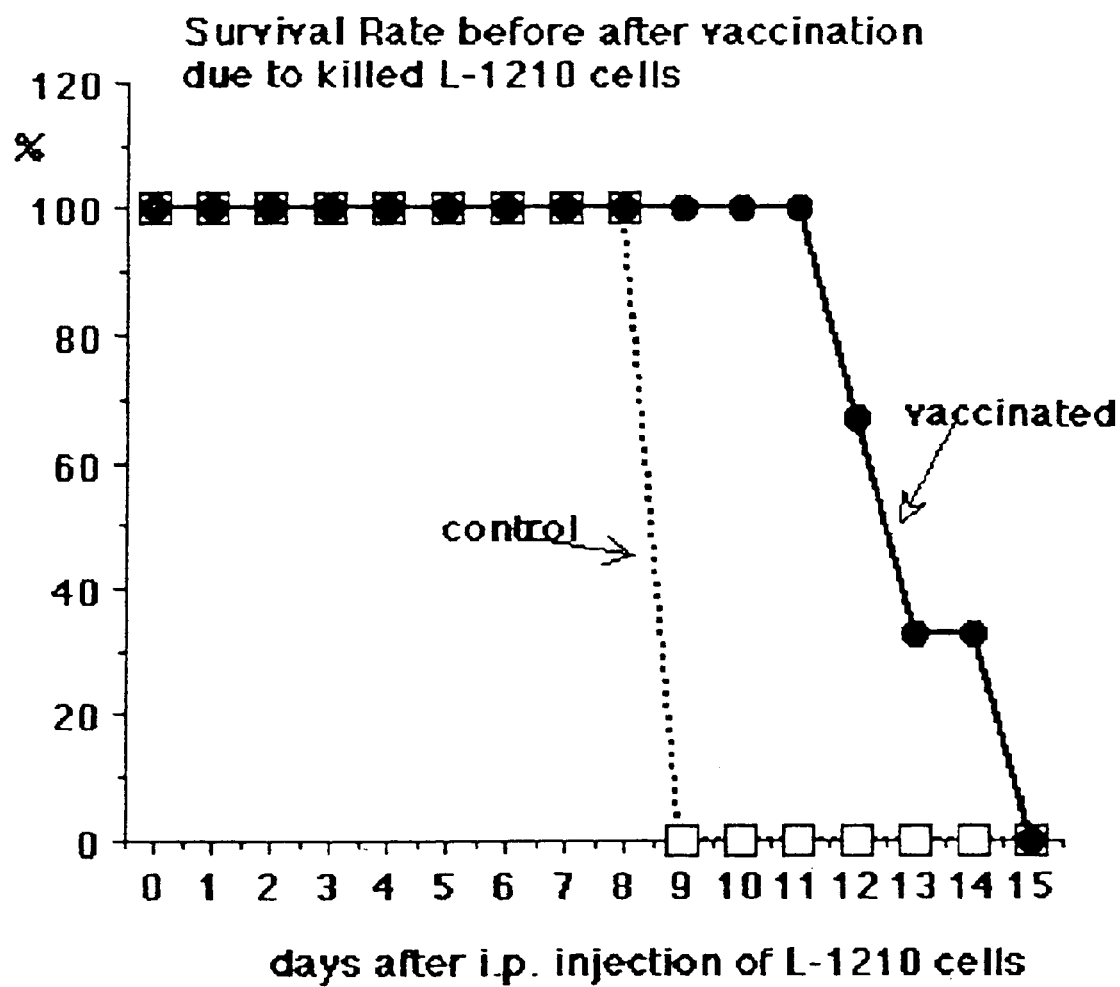

Peudomonas
treated serum control complex materials
treated serum control

US 7,914,793 B2

METHOD FOR PRODUCING AN ANTIGENIC SUBSTANCE AND ANTIBODY

This application is a continuation of application Ser. No. 09/881,664, filed Jun. 18, 2001 now abandoned, which is a continuation of application Ser. No. 09/355,642, filed Nov. 10, 1999, now abandoned which is a 371 of PCT/JP98/00351 filed Jan. 28, 1998.

TECHNICAL FIELD

This invention concerns vaccine precursor, vaccine, antibody, neutralizing antibody, antitoxin or idiotype antibody of which is able to discriminate substrates (lipid, carbohydrate, amino acid and so on) of less than molecular weight of 10,000. Such substrates consist of fundamentally morphological structure and/or physiological function and those form complex macromolecules of which are induced species-specific morphological and functional diversity. Either vaccine precursor, vaccine, antibody, neutralizing antibody, antitoxin or idiotype antibody is constituted by macromolecules substance more than one macromolecule. Also, this invention concerns vaccine precursor, vaccine, antibody, neutralizing antibody, antitoxin or the idiotype antibody induced by its idiotype antibody of which was mentioned above. In addition, this invention concerns anti-microbial agent, antiviral agent, anti-tumor agent, anti-protozoa agent (malaria, spirochaeta et. al), antitoxin, antibody of non-biological macromolecules, molecular discriminating agent, labeled compounds which has labeled substance or which has group including trace compounds being capable to demonstrate an effecting site, histo-compatible accelerator on homologous tissues or organs, histo-compatible accelerator on heterogeneous tissues or organs, accelerator of immuno-reaction or controller of immuno-reaction or accelerator of complement-linkage reaction.

PRIOR ART

Generally, a part of role on an immune system in organism is to usually defense normal functioning by recognizing an inconvenient substance for the organism which is generated to exclude outside to the organism. For example, this immune phenomenon relates to infectious defense of micro-organism, refusal of cell originated from different species, removal of mutational cells and/or damaged tissue. It is clear that this existence of antigen-antibody reaction has rescued lots of human life by vaccine and antitoxin as a preventive method. Utilizing this immunological mechanism, a first step of conventional cellular destruction for extracting antigenic substance from microorganism, infected cells with a microorganism and/or cancer cell to apply to live attenuated vaccine or inactivated vaccine has been used ultrasonic wave, freezing technique and combination with heat treatment. Moreover, it has been performed that addition of adjutants such as Al(OH) raises antibody titer after being inactivated antigen containing liquid, which was isolated by a centrifuged separation so on, by use of heat treatment, formaldehyde, paraformaldehyde or ultraviolet rays. However, application of heat, acid and alkaline treatments, and using of an organic solvent such as alcohol, ether, acetone or chloroform may cause chemical modification of molecular structure of the targeted antigen resulting in not only decrease in antigenicity but limitation of sufficient induction of immune mechanism with complexity and reasonability. Thus, it has been expected that development of antibody and/or vaccine which is capable to discriminate a targeted macromolecule existed in organism with specificity.

Generally, when antigen receptor (antigen acceptor) which exists on the surface of lymphocytes is encountered to an antigen which is "non-self", the antigen binds with the receptor (antigen recognition) resulting in a serial functioning of an elimination mechanism. This linkage has been well known to be specific. Moreover, it is known that this antigen receptor is one of protein molecules (polypeptides) which is induced by a gene and, that immunological specificity and immunological memory is created by a structure of the polypeptide with diversity. In other words, in order to promote antigen recognition efficiently and smoothly, lymphocytes produce and release a lot of antigen receptors to bind to acceptors (non-self). This antigen receptor which is released from the cell is called as an antibody. The many trials which utilize these antibodies artificially is one of central subjects in biological and medical research during this century and, many expected results have been provided. However, a diversity of antibody is astronomical. There are many problems to manipulate a targeted antibody artificially. Thus, it has been anticipated to be presented a demonstration with a new scientific concept.

Generally, it has been well known that a property of B cell is to have immunoglobulin on the surface. Immunoglobulin of the surface on the B cell is membrane-immuno-globulin with transmembrane portion, but not agglutination substance of antibody in blood (secretary immuno-globulin) and, it functions as B cell receptor to recognize a foreign substance (antigen). Activated B cell by that an antigen binds to B cell receptor differentiates to antibody secretary cell (plasma cell). In this case, a property of the produced antibody is to maintain a homologous antigenic specificity with the membrane immunoglobulin which exists on the surface of B cell. A important role of B cell in an immune system is to produce a specific antibody against an antigen. It is recently understood that diversity of an antibody, which is capable to correspond of numerous antigens with one by one, is generated in a gene level. This recent biological knowledge and technique have been expanded various developments, however, it is also anticipated to propose a method of an antibody production which does not depend on an analysis and determination of newly produced amino acid sequence by gene. In other words, an antibody production due to genetic engineering may spend a lot of time to identify a property of the antigen and to establish a production process. A production cost may become high. It is a reason to be discussed an economic efficiency and/or timely supply of an adequate vaccine when it is needed to use widely as an aim of public health care or prevention.

Immunoglobulin is formed of two components of heavy chain (H chain) and light chain (L chain) which has common amino acid sequence (common fragment; Fc) on the carboxyl terminal of each immunoglobulin, however, amino acid sequence of the amino terminal differs depending on each immunoglobulin. Antigen-recognition site of immunoglobulin is composed from a variable fragment of this H chain and L chain and, a difference of the amino acid sequence induces to produce a difference and diversity of antigen specificity is produced. Thus, although genetic domain cording the common fragment of each H chain and L chain is fixed on one domain, genetic domain cording the variable fragment is divided into some domains (segment). A combination of the segments results in the diversity of antibody. In other words, a paired part between one of H chain and L chain in antibody molecule is a segment which is called Fab, so that two Fab exists in the antibody. A position formed only by two H chains is a segment which is called Fc. Therefore, when an antibody molecule is displayed on a plane, antibody makes a Y shape with two Fab and one Fc1. It has been studied and performed energetically to develop vaccine and/or antibody corresponding to a difference of antigen specificity and structural specificity related to a generation of diversity.

A destruction of a cellular membrane is triggered by Fc segment of the antibody which has been linked with a cell. For this reason, Fc segment is an important segment. A kind of amino acids and sequence from an terminal end to middle part of Fab segment differs corresponding with each antigen. However, amino acids of Fc segment is quite identical even in different kind of antigen. A site which an antibody binds with an antigen (variable fragment) has a different structure corresponding with each antigen. Thus, when an animal is injected with the antibody, a different antibody is produced in an animal corresponding with each antigen. An antigen with a variable fragment which is able to discriminate is called as idiotype antibody. This idiotype antibody has been thought as an ideal antibody which may induce a better specificity of an antibody. Therefore, many researches and developments to find and/or produce this kind of antibody have been performed. Diversity of antibody is based on mini-gene system (family) which consists of more than 100 kinds of V (variable) genes, 12 of D (diversity) genes and 4 of J (joining) genes. Also, C (constant=permanent segment) gene is different depending on a function of the antibody and, this segment is not participated in a linkage with an antigen. During a differentiation to an antibody-produced cell, each gene is chosen from each mini-gene family so that V-D-J-C gene is completed by binding with each mini-gene family. The number of related gene are about 4,800 in H chain and about 400 of combination with mini-gene family of V, J and C in L chain. Thus, antigen-linkage segment to form a pair of H chain and L chain become a possibility of diversity with 4,800 times 400 (1,920,000) as a simple calculation. In addition, when gene is rearranged, several DNA codons may inserted into the binding site between V and D or between D and J by a special enzyme so that diversity of an antibody molecule enlarges astronomically. To induce antigen-antibody response corresponding with the diversity depending on species is reasonable. Thus, a simple induction, production technique and/or manufacturing and a definite demonstration has been expected.

Generally, a substance acting as an antigen is protein and/or bacterial toxin of different species of animals and individuals, protein of virus, proteins such as lipoproteins and glycoproteins of cellular membrane of different species of animals and individuals, lipids such as bacterial cell membrane and polysaccharides and/or lipopolysaccharides of bacterial membrane and blood-type substances. In addition, it has been known that artificially synthesized chemical substance becomes to have a capability of producing antibody against it's substance when the substance is linked to carrier and becomes to be antigenic determinant. A diazonized aromatic amino substrate (dinitrophennyl: DNP, trinitrophenyl: TNP, dinitrochlorobenzen: DNCB et al.) has been used for research as artificial antigen. In other words, when chemical substances and drugs, because of it's low molecule, are linked with a protein (carrier) because of it's low molecule, antibody which is enveloped chemical substance is produced. Thus, the chemical substance itself has not a capability of antibody production, however, when antibody is produced the low molecule substance being able to bind to the antibody when antibody is produced is called hapten. Then, a chemical substance which becomes a new hapten has been expected.

Many improvements are needed to prevent infectious diseases even at the present although peoples have been received the benefit and favor from conventional techniques and clinical application. For example, the influenza which is one of viral infection is related to a primary proliferation on the airway. Moreover, a viral infection such as measles, mumpus and/or chicken pox becomes to onset it's symptom when a virus is proliferated in the blood resulting in expanding into the body after the airway infection. In addition, a virus such as hepatitis and Japanese encephalitis becomes to onset diseases resulting from a proliferation after reaching to the targeted organs via blood stream. Those infections may be able to prevent onset of illness if a neutralizing antibody exists into the blood. Recently, a risk of microbial infection such as HIV, hepatitis virus and/or ebora virus still exists. Prevention of those infectious diseases has been done by immunization injecting a non-pathogenic or inactivating viral antigen against the virus as a preventive method of viral infection. As one of methods, an efficacy of an inactivated vaccine which is made by killed virus and live attenuated vaccine has been well known. Also, an effectiveness of an inactivated vaccine such as Japanese encephalitis virus, hepatitis virus and polyomyelitis virus has been suggested. However, in general, it has been known that an effect of live attenuated vaccine is better than that of an inactivated vaccine. Vaccine against a virus of measles, rubella, mumpus, chicken pox and polyomyelitis has been applied as live attenuated vaccine. Difficult acquisition of antigen such B typed hepatitis and hazardous handling is resolved by antigen is produced in bacterium resulting from recobination of antigen gene into the bacterial DNA. Recombinant DNA-induced vaccine has been manufactured safely, and has been tested energetically on antibody against HIV. A new type of vaccine such as vector-vaccine and idiotype vaccine is also expected: the former one is to preserve immunity by recombinating gene of a objective virus into a non-pathogenic virus, and later one to utilize anti idiotype antibody which may have an identical structure of the antigen.

Suppurative bacteria (*Stapylococcus, Streptococcus peumonia, Pseudomonas aureginosa, Eschericia coli* et al.) are treated with immuno-bacteriolysis phenomenon induced by phagocytosis and/or bactericidal action of neutrophils or with activated complement. Bacteria has a substance which resists to phagocytosis on capsule of *Diplococcus pneumonia*, M-protein of *Streptococcus* and mucoprotein of *Streptococcus*, and a dangerous bacteria which has exotoxin such as *E. coli* 0-157, Shigella, Cholera exists. Toxin produced by those *bacilli* (tetanus exotoxin and diphtheria exotoxin et al.) is be able to be neutralized by binding with antibody against those toxins. A major immuno-globulin is antibody belongs to IgG. Also, bacteria such as tuberculosis, leprosy, salmonella, listeria is resistance to bactericidal effect so that neutrophilic cell itself is not able to kill because of it's short-life span. Thus, phagocytosis and sterilization effect of macrophages is needed. Macrophage-activating factor which is one of lymphokaines produced by T cell after responding to antigen is important. And, it's immune bacteriolysis phenomenon affects efficiently on gram-negative bacteria. Namely, in order to the prevention of Neisseria (*N. meningococcus* and *N. gonorrhoeae*), this mechanism is an important mechanism. This mechanism is activated by alternative pathway which complement affects on surface substance of bacteria, however, an activation of classical pathway through antibody linked with bacteria (especially IgM. IgG) is more effective. It has been anticipated that new vaccine and antibody against those bacilli is developed. In addition, for example, B-typed hepatitis vaccine is produced by S-antigen of B-typed hepatitis virus, of which materials is used from serum with S-antigen positive subject (HB virus carrier). However, this manipulation is restricted by supply of the materials, has a possible risk of infectious focus from serum and is accompanied with a hazard for the handling. As the means which resolve this problem, by a gene recombination technique, a gene of S-antigen is introduced in microbial DNA such as *E. coli* and yeast so that a introduced microorganism becomes to produce S-antigen. The method with an availability has been widely developed at the present that when lots of the recombined bacteria are cultured, lots of S-antigen is obtained. This is one of examples in development and application of DNA recombinant vaccine. Also, if amino acid sequence of gene DNA related to antigen is defined, it is technically possible to chemically synthesize antigen-peptides on basis of the sequence resulting in a production of synthesized peptide-antibody. However, immunogenic potency of synthetic peptide alone as a antigen mentioned above is weak so that any kinds of adjuvants is needed to add. Thus, it has been expected a proposal and/or possibility in concrete form and easy procedure, which those structures such as proteins and saccharide chains are able to approximate more closely to an objected antibody.

It is possible to induce antigen of the objective virus on virus which safety has been already confirmed and which is recombinated gene of a targeted idiotype antigen. When the former virus which has confirmed safety is used as vaccine, it is possible to induce an immunity against the later virus at the same time. These vaccines are a kind of vector vaccines so that vaccine which is produced HA-antigen of influenza into vaccinia virus is utilized as a vaccine recombinated antigen-gene of other virus instead of application of idiotype antigen. However, this method is not capable to apply to all kinds of virus although a strain of virus is safe so that it is most difficult to find out vector virus which is preserved a safety adequately against each targeted virus. At an emerging situation, it is hard to supply vaccine temporally, economically and technically. Thus, it has been anticipated to resolve and/or improve those several subjects concerning on conventional vaccine.

Complement plays a role of killing or phagocytosing pathogens resulting from contact directly or indirectly with pathogens. Complement is capable to act directly on bacteria and to be activated by mannose-binding protein. Furthermore, as a result of infection, the produced antibody is able to activate complement so that the activated complement causes an extinction of bacteria or induces immunological phagocytes such as macrophages and/or neutrophils. On bacteria which causes pneumonia or pharyngitis, capsule consisted of long saccharide chain protects a direct action of complement to bacteria. A shape of this mannose-binding protein is altered when it binds to bacteria, resulting in an activation of complement and an promotion of activating phagocytosis. However, although it has known that functional induction and/or generation differs corresponding with different linkage of saccharide chain with a same protein structure, it is very difficult to produce and manufacture glycoproteins with specific action gene-technologically by use of conventional techniques because of biological diversity. It has been anticipated to manufacture and/or demonstrate specific vaccine, antibody, antitoxin and neutralizing antibody which are induced by extracting those species-specific glycoproteins.

And, it is indicated that cells which become tumor have an abnormal metabolism so that there is a possibility of abnormal synthesis of a substance on cell membrane, namely saccharide chain. This abnormality has two possible pathways; a partial synthesis which is not able to synthesize whole length of the saccharide chain, and an extreme different production of saccharides. Those saccharides chain become a tumor-related antigen so that because of short length of molecule, a shortly synthesized saccharide is easily coated the cell surface by a substance and is less effective. Moreover, a possibility has been indicated that substances such as siarylmutin, hyaluronic acid and chondroitin sulfate exist on the surface of tumor cells so that the tumor-related antigen is covered by those substances resulting in dysfunctioning an immune-response. Thus, a proposal of an effective method which increases an induction-rate of tumor-related antigen is expected, accompanied with a trial of prevention and/or treatment against malignant tumors in order to improve an immunological dysfunction due to abnormality of saccharide chain and to scavenge smoothly tumor-induced cells in vivo.

HIV is one of major infectious diseases which has been a world-wide topic. Recently, a treatment depending on only one mechanism of HIV infection has been thought to be difficult to prevent HIV. Generally, virion of HIV (particle of virus itself) is roughly globular and it's diameter is 100 nm. Outer membrane consisted with bilayer of lipid molecule (outer capsule or envelope) is similar to human cellular membrane and identical to evolutional origin. A spike consists of four glycoproteins of gp120 (gp means glycoproteins). Those proteins of envelope play an important role of binding to cells resulting in invasion into a target cell. A layer of matrix-protein which is called as p17 exists just below the envelope. Capsid consists of another kind of proteins called as p24. These double strands of RNA is constituted by about 9,200 base pairs and becomes compact completely into the core of virus. Glycoprotein (gp120) of envelope binds hardly to CD4. Therefore, antibody which recognizes gp120 and gp41 on envelope of HIV binds CD4 as well as those proteins bind a MHC molecule on the surface of healthy cell, resulting in a disturbance of immunological function. Both gp120 and gp41 has a similar amino acid sequence to MHC molecule. It has been developed and tested various kinds of drugs by those biological properties, however, a stage of medicare and/or treatment is not sufficient. Namely, it has been required for a medical prevention to develop a effective vaccine such as an antibody of special glycoproteins of HIV, although it has been speculated that many carriers exist.

Though it is not necessary to do more than to read history of relationship between a man and diseases, a fighting to pathogenic microbacterial infection such as bacteria and virus, it is serious problems which needs a medical resolution. Various kinds of pathogenic microbacteria such as staphylococcus aureus, streptococcus, *E. Coli*, acid-fast bacteria, mycete and virus usually exist on the living space of human being as origin of various infectious diseases. Thus, lots of drugs are utilized in a treatment and prevention for infectious disease due to pathogenic microorganism and virus. As a result, lots of the benefits have been raised However, while development of antibacterial agents is noticeable, it has been expected in the field of hygenical and preventative medicine to develop an effective vaccine against wide-spreaded group infections.

It is not sufficient to accept a conventional idiotyped vaccine and/or antibody at the present, although it has been indicated that as a scientific knowledge multidimensional structure of biological substance mentioned above is important to generate various biological functions, and that as an acceptable proposal idiotype vaccine and/or antibody being applied structural diversity on the basis of species-differented cellular specificity in order to be induced functional diversity by multidimensional structure is logical. It is anticipated to be demonstrated a simple method of the simplicity and concrete manufacture and or a performed example. It is a important issue which has been expected as an advanced technology even in the field of a practical medical service which is faced directly on human life as well as in the academic field of biology, chemistry and medicine.

On the other hand, for example, elements of living organism consist of lipids, carbohydrates, proteins, enzymes, nucleic acids, macromolecules such as amino acids and peptides and genes (for example, DNA, tRNA, mRNA, rRNA). By those elements, in addition, formation of cell membrane, intracellular organelle, intracellular and/or extracellular substrates are constructed. Function of these complex substances is generated by multidimensional structure (conformation) depending on each substance. In order to understand the mechanism which is related to development and generation of each physiological function (recognition and/or acceptance of substance), it is important to understand the multidimensional structure which each substance has. (ed. by Alberts, Bray, Lewis, Raff, Roberts and Watson, The Molecular Biology of the CELL, Garland Publishing Inc., 3th. edition <ref. 2>). A state of charge distribution and electric charge density of molecules which consist of substances and is generated function by these multidimensional structure differs in species differences and morbidity <ref. 2>. In addition, virus, which has not cell membrane and is not living organism, consists of peptides chain which are constructed by many amino acid bindings. And, these virus particles have also multidimensional structure such as two-dimension and/or three-dimension. Among multidimensional structure, helical structure is formed in 3.6 amino acid residues per one helical rotation. Thus, it produces a space which side chain can occupy. And, possible hydrogen bonds on this helical structure can be constituted totally. In addition, multidimensional structure generates the function of α domain, beta domain, α/beta domain, exon or intron. This concept is also a scientific fact and important knowledge. Though a core part of this structure is conserved in homologous proteins, dimensional changes in a helix loop region occur. Moreover, formation of conformation depends on a type of the secondary structure to bind each loop and a number of amino acids in helix loop rather than amino acid sequences. Therefore, it is in general to be determined by combination of α-α, beta-beta, α-beta or beta sheet-α loop. These multidimensional structure is to apply to molecular biology of every kinds of genes and antibodies from recent knowledge. It is well known scientific fact and knowledge that it is important to generate physiological function based on recognizing two- or three-dimensional conformation of each substance <ref. 2>. It has been raised to produce and/or synthesize an artificial substance which responds specifically against each substance, as well as to exactly resolve a function of organism. And, it has been anticipated to develop a method related on treatment and/or medical care on the basis of a knowledge concerned on biological functions of organism with a diversity and species-specificity, resulting from integrating many combinations with those substances.

On a biological fact mentioned above, it has been expected to develop and/or provide the following substances with higher specificity and/or selectivity: vaccine precursor, vaccine, antibody (including idiotype antibody), neutralizing antibody, antitoxin, or anti-microbial agent, antiviral agent, anti-tumor agent, anti-protozoa agent (malaria, spirochaeta et. al), molecular discriminating agent, antibody with a labeled compound, anti idiotype antibody and/or histocompatible accelerator on homologous tissues or organs, histocompatible accelerator on tissues or organs, accelerator of immuno-response, controller of immuno-response or accelerator of complement-linkage reaction. Those include substances of which are produced by its idiotyped antibody. Those proposed substances with fundamental conformation are able to block and/or inhibit multi-dimensionally generated functions of biological or non-biological complex macromolecules, and to induce non-functioning of such macromolecules.

An object of this invention is to resolve the problems mentioned above and to provide the following substances with a higher recognizing property of a targeted acceptor-substance: vaccine precursor, vaccine, antibody (including idiotype antibody), neutralizing antibody, antitoxin, or anti-microbial agent, antiviral agent, anti-tumor agent, anti-protozoa agent (malaria, spirochaeta et. al), molecular discriminating agent, antibody with a labeled compound, anti idiotype antibody and/or histocompatible accelerator on homologous tissues or organs, histocompatible accelerator on tissues or organs, accelerator of immuno-response, controller of immuno-response or accelerator of complement-linkage reaction. Those include substances of which are produced by its idiotyped antibody. And, those substances and/or compounds are produced and/or manufactured by a simple technique. And, those are similar to the original elements of generating a diversity of species such as a specificity and/or selectivity as far as possible.

In order to achieve to the objectives mentioned above, the inventors have efforted to investigate. This invention indicates a possible production of the following substances: vaccine precursor, vaccine, antibody (including idiotype antibody), neutralizing antibody, antitoxin, antibody with a labeled compound. This invention also discloses beneficial effect of antibody of which is anti-microbial agent, antiviral agent, anti-tumor agent, anti-protozoa agent (malaria, spirochaeta et. al), anti idiotype antibody and/or histocompatible accelerator on homologous tissues or organs, histocompatible accelerator on tissues or organs, accelerator of immuno-response, controller of immuno-response or accelerator of complement-linkage reaction. Those findings are based on effects of granulizing and dispersing cells as anti-microbial agents, anti-fungal agents, anti-viral agents, bactericidal and/or sterilized agents and anti-tumor agent of antigenic substance inductor. Additionally, those findings are based on effects as antigen-antibody reaction, reductants, free radical scavengers, desulfurization agents, depolymerization agents, copolymerization agents, improving agents for functional and/or physical property with surface active substances and/or surfactants, improving agents of microphase separation structure and phase transition agents or improving agents of phase transition of antigenic substance inductor. A production of antibody of non-biological macromolecules is also possible.

CONSTITUTION OF THE INVENTION

The invention in a first embodiment in order to accomplish above-mentioned purpose is antigenic substance inductors which are capable to produce and/or manufacture vaccine precursor, vaccine, antibody, neutralizing antibody, antitoxin and idiotype antibody. The invention in a second embodiment is a vaccine precursor, vaccine, antibody, neutralizing antibody, antitoxin, and idiotype antibody of which is produced and/or manufactured by using of those antigenic substance inductors. The invention in a third embodiment is a vaccine precursor, vaccine, antibody, neutralizing antibody and antitoxin of which is produced and/or manufactured by using of its idiotype antibody. The invention in a fourth embodiment is anti-idiotyped antibody induced by vaccine precursor, vaccine, antibody, neutralizing antibody, antitoxin or idiotype antibody of the second and third embodiments as artificial antibody of non-biological macromolecular substance (peptides, proteins, lipids, glycoproteins, glycolipids, polysaccharides et al.), anti-microbial agent, antiviral agent, anti-tumor agent, anti-protozoa agent (malaria, spirochaeta et. al). The invention in a fifth embodiment is antibody or idiotype antibody of the second embodiment as molecular discriminating agent, labeled tracers substituted an acting site, including substance which becomes to be a labeling of demonstrating an acting site or with a trace, histocompatible accelerator on homologous and/or heterogeneous tissues or organs, accelerator of immuno-reaction, controller of immuno-reaction or accelerator of complement-linkage reaction.

A fundamental principle of this invention is to obtain a biological capacity of antibody recognition by utilizing granulized and/or fragmented structural substance as a result of extinction of microorganism, virus, tumor cell (cancer cell) and protozoa (malaria, spirochaeta et. al). This mechanism of fragmentation results from a quantum thermodynamic disruptive and fragmented effects of antigenic substance inductors. Moreover, the first objective of this invention is to generate an effective function of antibody utilized by the above quantum thermodynamic effects of antigen substance inductors. Second is to produce and/or manufacture antibody such as attenuated vaccine, inactivated vaccine, neutralizing antibody, antitoxin and artificial antibody. Another effects of the antigenic substance inductors have been published in the International Publication No. WO96/07403 related on inhibitory or blocking agents of molecular generating and/or inducing functions as well as its synthesizing manipulation.

The antigenic substance inductor according to the present invention contains as an effective ingredient the compound represented by the Formulae below.

Formula 1-a recited in claim 1 is

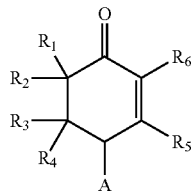

Formula 1-a (wherein
(i) R1, R2, R3, R4, R5 and R6 represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;
(ii) A represents hydrogen atom or

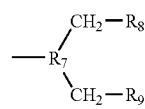

(wherein
R7 represents C1-C6 alkyl group; sulfide group or phosphate group;
R8 and R9 represent independently hydrogen atom; halogen atom; straight or branched C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group; (iii) one or more of R1, R2, R3 and R4, and/or one or more of R5 and R6 may be substituted or non-substituted cyclopentyl group; substituted or non-substituted cyclohexyl group; or substituted or non-substituted naphthyl group; (iv) R5 and R6 may form a ring by binding with another condensation polycyclic hydrocarbon compound or heterocyclic compound; (v) one or more of R3, R4, R5 and R6 may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group; (vi) R2 and/or R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group; (vii) when one or more of R3, R4, R5 and R6 are alkyl groups, terminal end(s) of the alkyl group(s) may be substituted by C3-C8 cycloalkyl group).

In general formula 1-a, aryl group in (i), (ii) and (v) which was mentioned above represents phenyl, tolyl, xylyl or naphthyl group. The substituted cyclopentyl group in (iii) which was mentioned above is cyclopentylamino group or cyclopentylcarbinol group. The substituted cyclohexyl group of which was mentioned above represents cyclohexylamino group, cyclohexylaldehyde group or cyclohexyl acetic acid group. The substituted naphthyl group of which was mentioned above represents naphthyl amino group or naphthylamino sulfonic acid group. Condensation polycyclic hydrocarbon compounds in (iv) which was mentioned above represents pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene. The compounds of heterocyclic group which was mentioned above represents furan, thiophene, pyrrole, ■-pyran, ■-thiopyran, pyridine, thiazole, imidazole pyrimidine, indole or quinoline.

Formula 1-b is

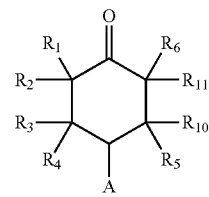

Formula 1-b (wherein
(i) R1, R2, R3, R4, R5, R6, R10 and R11 represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group;
(ii) A represents hydrogen atom or

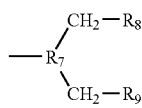

(wherein
R7 represents C1-C6 alkyl group; sulfide group or phosphate group;
R8 and R9 represent independently hydrogen atom; halogen atom; straight or branched C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group; (iii) one or more of R1, R2, R3 and R4, and/or one or more of R5, R6, R10 and R11 may be substituted or non-substituted cyclopentyl group; substituted or non-substituted cyclohexyl group; or substituted or non-substituted naphthyl group; (iv) R5, R6, R10 and R11 may form a ring by binding with another condensation polycyclic hydrocarbon compound or heterocyclic compound; (v) one or more of R3, R4, R5, R6, R10 and R11 may be substituted by one or more of substituents selected from the group consisting of halogen atom, cyano group, protected or non-protected carboxyl group, protected or non-protected-hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group; (vi) R2 and/or R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group; (vii) when one or more of R3, R4, R5, R6, R10 and R11 are alkyl groups, terminal end(s) of the alkyl group(s) may be substituted by C3-C8 cycloalkyl group).

In general formula 1-b, Aryl group in (i), (ii) and (v) which was mentioned above represents phenyl, tolyl, xylyl or naphthyl group. The substituted cyclopentyl group in (iii) which was mentioned above represents cyclopentylamino group or cyclopentylcarbinol group. The substituted cyclohexyl group of which was mentioned above represents cyclohexylamino group, cyclohexylaldehyde group or cyclohexyl acetic acid group. The substituted naphthyl group of which was mentioned above represents naphthyl amino group or a naphthylamino sulfonic acid group. Condensation polycyclic hydrocarbon compounds in (iv) which was mentioned above represents pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene. The compounds of heterocyclic group which was mentioned above represents furan, thiophene, pyrrole, ■-pyran, ■-thiopyran, pyridine, thiazole, imidazole pyrimidine, indole or quinoline.

Formula 2 is

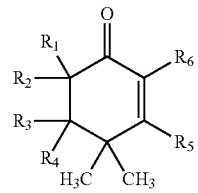

Formula 2

(wherein
(i) R1, R2, R3, R4, R5 and R6 represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group; (ii) one or more of R1, R2, R3 and R4, and/or one or more of R5 and R6 may be substituted or non-substituted cyclopentyl group; substituted or non-substituted cyclohexyl group; or substituted or non-substituted naphthyl group; (iii) R5 and R6 may form a ring by binding with another condensation polycyclic hydrocarbon compound or heterocyclic compound; (iv) one or more of R3, R4, R5 and R6 may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group; (v) R2 and/or R5 may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group; (vi) when one or more of R3, R4, R5 and R6 are alkyl groups, terminal end(s) of the alkyl group(s) may be substituted by C3-C8 cycloalkyl group).

In general formula 2, aryl group in (i) and (iv) which was mentioned above represents phenyl, tolyl, xylyl or naphthyl group. The substituted cyclopentyl group in (ii) which was mentioned above represents cyclopentylamino group or cyclopentylcarbinol group. The substituted cyclohexyl group of which was mentioned above represents cyclohexylamino group, cyclohexylaldehyde group or cyclohexyl acetic acid group. The substituted naphthyl group of which was mentioned above represents naphthyl amino group or a naphthylamino sulfonic acid group. Condensation polycyclic hydrocarbon compounds in (iii) which was mentioned above represents pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene. The compounds of heterocyclic group which was mentioned above represents furan, thiophene, pyrrole, ■-pyran, ■-thiopyran, pyridine, thiazole, imidazole pyrimidine, indole or quinoline.

Formula 3-a is

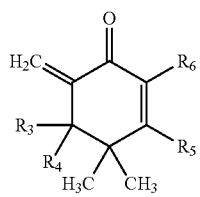

Formula 3-a (wherein
(i) $R_3$, $R_4$, $R_5$ and $R_6$ represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group; (ii) one or more of $R_3$ and $R_4$, and/or one or more of $R_5$ and $R_6$ may be substituted or non-substituted cyclopentyl group; substituted or non-substituted cyclohexyl group; or substituted or non-substituted naphthyl group; (iii) $R_5$ and $R_6$ may form a ring by binding with another condensation polycyclic hydrocarbon compound or heterocyclic compound; (iv) one or more of $R_3$, $R_4$, $R_5$ and $R_6$ may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group; (v) $R_5$ may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group; (vi) when one or more of $R_3$, $R_4$, $R_5$ and $R_6$ are alkyl groups, terminal end(s) of the alkyl group(s) may be substituted by C3-C8 cycloalkyl group).

In general formula 3-a, aryl group in (i) and (iv) which was mentioned above represents phenyl, tolyl, xylyl or naphthyl group. The substituted cyclopentyl group in (ii) which was mentioned above represents cyclopentylamino group or cyclopentylcarbinol group. The substituted cyclohexyl group of which was mentioned above represents cyclohexylamino group, cyclohexylaldehyde group or cyclohexyl acetic acid group. The substituted naphthyl group of which was mentioned above represents naphthyl amino group or a naphthylamino sulfonic acid group. Condensation polycyclic hydrocarbon compounds in (iii) which was mentioned above represents pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene. The compounds of heterocyclic group which was mentioned above represents furan, thiophene, pyrrole, ■-pyran, ■-thiopyran, pyridine, thiazole, imidazole pyrimidine, indole or quinoline.

Formula 3-b is

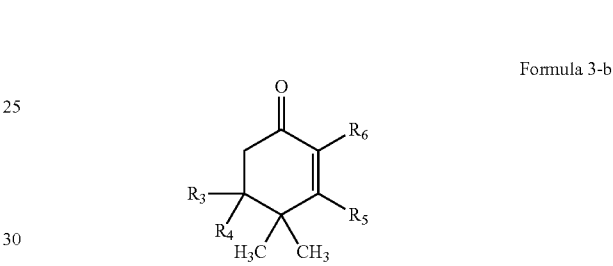

Formula 3-b (wherein
(i) $R_3$, $R_4$, $R_5$ and $R_6$ represent independently hydrogen atom; halogen atom; C1-C6 alkyl group; amidino group; C3-C8 cycloalkyl group; C1-C6 alkoxy C1-C6 alkyl group; aryl group; allyl group; aralkyl group in which one or more C1-C6 alkyl groups are bound to an aromatic ring selected from the group consisting of benzene, naphthalene and anthracene ring; C1-C6 alkylene group; benzoyl group; cinnamyl group; cinnamoyl group or furoyl group; (ii) one or more of $R_3$ and $R_4$, and/or one or more of $R_5$ and $R_6$ may be substituted or non-substituted cyclopentyl group; substituted or non-substituted cyclohexyl group; or substituted or non-substituted naphthyl group; (iii) $R_5$ and $R_6$ may form a ring by binding with another condensation polycyclic hydrocarbon compound or heterocyclic compound; (iv) one or more of $R_3$, $R_4$, $R_5$ and $R_6$ may be substituted by one or more of substituents selected from the group consisting of halogen atom, cyano group, protected or non-protected carboxyl group, protected or non-protected hydroxyl group, protected or non-protected amino group, C1-C6 alkyl group, C1-C6 alkoxy group, C1-C7 alkoxy carbonyl group, aryl group, C3-C6 cycloalkyl group, C1-C6 acylamino group, C1-C6 acyloxy group, C2-C6 alkenyl group, C1-C6 trihalogenoalkyl group, C1-C6 alkylamino group, and C1-C6 dialkylamino group; (v) $R_5$ may be substituted by one or more substituents selected from the group consisting of halogen atom, C1-C6 alkyl group, protected or non-protected carboxyl group, protected or non-protected hydroxyl group, protected or non-protected amino group, protected or non-protected C1-C6 alkylamino group, protected or non-protected C1-C6 aminoalkyl group, protected or non-protected C1-C6 alkylamino C1-C6 alkyl group, protected or non-protected hydroxyalkyl group, and C3-C6 cycloalkylamino group; (vi) when one or more of R3, R4, R5 and R6 are alkyl groups, terminal end(s) of the alkyl group(s) may be substituted by C3-C8 cycloalkyl group).

In general formula 3-b, aryl group in (i) and (iv) which was mentioned above represents phenyl, tolyl, xylyl or naphthyl group. The substituted cyclopentyl group in (ii) which was mentioned above represents cyclopentylamino group or cyclopentylcarbinol group. The substituted cyclohexyl group of which was mentioned above represents cyclohexylamino group, cyclohexylaldehyde group or cyclohexyl acetic acid group. The substituted naphthyl group of which was mentioned above represents naphthyl amino group or a naphthylamino sulfonic acid group. Condensation polycyclic hydrocarbon compounds in (iii) which was mentioned above represents pentalene, indene, naphthalene, azulene, heptalene, biphenylene, indacene, acenaphthylene, fluorene, phenalene, phenanthrene, anthracene, pentacene, hexacene, dibenzophenanthrene, 1H-cyclopentacyclooctene or benzocyclooctene. The compounds of heterocyclic group which was mentioned above represents furan, thiophene, pyrrole, ■-pyran, ■-thiopyran, pyridine, thiazole, imidazole pyrimidine, indole or quinoline.

Chemical effects and those logical mechanism of each antigenic substance inductor mentioned above has been already published in International Publication No. WO96/07403. This invention here indicates that a manipulation with each antigenic substance inductor is able to induce more specific recognition of biological substances as mentioned below. In addition, this invention indicates a possibility to produce a specific neutralizing antibody of toxin in vivo after pretreatment with its toxin in vitro. These vaccine precursor, vaccine, antibody, neutralizing antibody, antitoxin and idiotype antibody are utilized an inhibitory action of functions such as adhesive substance and/or signal transmission on virus, bacteria and cellular surface. Also, those are utilized an inactivated action and/or destroying effect on envelope of virus and/or bacterial or cellular membranes followed by a quantum thermodynamic property of antigenic substance inductor mentioned in this invention. Thus, it is possible to inactivate and/or attenuate adhesive substances, signal transmitters and/or toxins of virus, protozoa, bacteria and/or tumor cells. The inductor provides a more preserved fundamental topological structure (conformation), even when antigenic substance inductors mentioned in this invention are applied by a similar handling to organic solvents such as formalin or paraformaldehyde on a conventional inactivation or attenuation processes of vaccines. Moreover, a degree of attenuation, inactivation and/or extinction by antigenic substance inductors mentioned in this invention can be controlled by a dosage or concentration.

Moreover, it is obvious that future scientific discussions may resolve a further more details concerning on humoral antibodies in blood and/or antibodies existed on cellular membranes on a basis of this invention. In other words, antibody production and/or manufacture mentioned in this invention involves in a basic or fundamental concept to promote a future research and development activities to induce higher specificity of a biological self-recognition. For example, if a targeted complex macromolecule is identified, the molecule can be purified and condensed by biogenetic technique and/or cell fusion technique utilizing cDNA cloning from mRNA. Coming from the disclosure of this invention, it is also obvious that there are many possibilities and availabilities above examples demonstrated in this invention. In addition, a production process of a specific neutralizing antibody of toxin is able to make a less risk of secondary infections. A reason is that an induction of biological recognition in vivo is handled a toxin in vitro.

Coming from the disclosure of this invention, it is obvious to produce monovalent vaccine, combined vaccine (which consisted of various types of cells), cross-reactive vaccine according to an expected effect on samples of various pathological tissues and/or organs. Those samples are infected by prion, virus, rickettsia or microorganisms, and invaded by tumor cells. In addition, those samples are pathological tissues and/or organs of unknown caused diseases (namely, intractable diseases). Thus, antigenic substance inductor mentioned in this invention does not lose a fundamental structure (conformation) depending on species resulting in a production and/or induction of multiple antibodies according to biochemical components evolutionary closed to species, and resulting in a production and/or induction of multifunctional antibodies (a diversity of antibody recognition) which are able to recognize multiple antibodies.

Additionally, coming from the disclosure of this invention, it is also obvious with a reasonability to accumulate a synergistic therapeutic efficiency. When antigenic substance inductor (preventative dosage or less than lethal dosage) is given at an onset of bacterial infections and/or tumor (cancer) in vivo, these constituted elements (granules and/or particles) extincted cells become to stimulate immune system of the host and to produce an antibody, so that further proliferation and invasion in vivo as a circulus vitiosus is blocked by this positive feed-back mechanism. This is to amplify an inactivated vaccine in vivo. This method is able to apply into preventive techniques for such diseases. Also, obviously, non-biological substances can apply as a kind of antibody catalysts.

Moreover, on each extracted substance by a processes mentioned in this invention, it is permissible to receive a further detoxification with ultraviolet irradiation, heating and/or conventionally used organic solvents such as aldehyde.

One or both terminals of each structure (mainly, amino terminal and carboxyl terminal) of vaccine precursor, vaccine, antibody, neutralizing antibody, antitoxin or idiotype antibody and, vaccine, antibody, neutralizing antibody or antitoxin which is induced by this idiotype antibody, molecular discriminator, and histocompatible accelerator, which is manufactured and/or produced by antigenic substance inductor according to the present invention, is substituted by more than one substituent as the follow. Those are chosen from substituent group consisting of halogen atom, cyano group, protecting carboxyl group, protecting hydroxyl group, protecting amino group, protecting alkyl group, protecting alkoxy group, protecting alkoxy carbonyl group, protecting aryl group, protecting cycloalkyl group, protecting acylamino group, protecting acyloxy group, protecting C2-C6 alkenyl groups, protecting C1-C6 trihalogenoalkyl group, protecting C1-C6 alkylamino group, protecting C1-C6 dialkylamino group, protecting C1-C6 aminoalkyl group, protecting C1-C6 alkylamino C1-C6 alkyl group or protecting cycloamino C1-C6 alkyl group.

However, if a special excuse is not appealed in the detailed description of this invention, the following representation is included here: halogen atom represents fluorine atom, chlorine atom, bromine atom or iodine atom as an example. Alkyl group represents C1-10 alkyl group such as methyl group, ethyl group, n-propyl group, isopropyl group, n-butyl group, isobutyl group, sec-butyl group, tort-butyl group, benzyl group, hexyl group or octyl group and so on as an example. Alkyl group with several carbon atoms (preferably C1-C6)

represents C1-5 alkyl group in alkyl group of which is mentioned above. Alkoxy group represents —O-alkyl group (alkyl group is C1-10 alkyl group mentioned above). Alkylamino group with several carbon atoms (preferably C1-C6) represents C1-5 alkylamino group such as methylamino group, ethylamino group or propylamino group and so on as an example. Dialkylamino group with several carbon atoms (preferably C1-C6) represents C1-5 dialkylamino group such as dimethylamino group. Alkenyl group with several carbon atoms (preferably C1-C6) represents C2-5 alkenyl group such as vinyl group, allyl group, 1-propenyl group or 1-butenyl group as an example. Cycloalkyl group represents C3-6 cycloalkyl group such as cyclopropyl, cyclobutyl, cyclopentyl or cyclohexyl as an example. Aryl group represents phenyl group or naphthyl group as an example. Alkoxy carbonyl group represents —COO-alkyl group (alkyl group represents C1-10 alkyl group above mentioned). Hydroxy alkyl group with several carbon atoms (preferably C1-C6) represents hydroxy-C1-5 alkyl group such as hydroxy methyl group, hydroxy ethyl group or hydroxy propyl group as an example. Amino alkyl group with several carbon atoms (preferably C1-C6) represents amino C1-5 alkyl group such as aminomethyl group, aminoethyl group or aminopropyl group as an example. Akyl group with several carbon atoms (preferably C1-C6) of alkylamino group with several carbon atoms (preferably C1-C6) represents C1-5 alkylamino C1-5 alkyl group such as methylaminomethyl group, ethylaminomethyl group or ethylaminoethyl group as an example. Alkyl group with several carbon atoms (preferably C1-C6) of dialkylamino group with several carbon atoms (preferably C1-C6) represents C1-5 dialkylamino C1-5 alkyl group such as dimethylaminomethyl group or diethylaminomethyl group. Cyclic amino group represents cyclic amino group with 4-10 membered ring such as piperazinyl group, 1,4-diazabicyclo (3,2,1) octyl group or morpholinyl group as an example. Alkyl group with several carbon atoms (preferably C1-C6) of cyclic amino group represents C1-5 alkyl group of cyclic amino group with 4-6 membered-ring such as 1-piperazinylmethyl group, 1-pyrrolidinylmethyl group, 1-azethydinylmethyl group or 1-morpholinylmethyl group as an example. Acylamino group represents C1-4 acylamino group such as formylamino group, acetylamino group, propionylamino group or butyrylamino group as an example. Acyloxy group represents C1-4 acyloxy group such as formyloxy group, acetyloxy group, propionyloxy group or butyryloxy group as an example. Trihalogeno-alkyl group with several carbon atoms (preferably C1-C6) represents trihalogeno C1-5 alkyl group such as trichloromethyl group or trifluoromethyl group as an example. Polycyclic group represents 5 membered-ring, 6 membered-ring or those condensation rings (such as furyl, propyl, thienyl, oxazolyl, imidazolyl, thiazolyl, 1-pyrrolinyl, benzofuryl, benzothiazolyl, pyridyl, quinolyl, pyrimidinyl or morpholinyl group as an example) which has more than one atom chosen from oxygen atom, nitrogen atom or sulfur atom.

Pharmaceutically permissible protecting substituents of carboxyl group with easily removal from body represents protecting carboxyl group such as esterized substituent.

Moreover, pharmaceutically permissible protecting substituents of amino group with easily removal from body are the follow: alkyl group with several carbon atoms of amino group and alkyl group with several carbon atoms of alkylamino group with several carbon atoms.

In addition, pharmaceutically permissible protecting substituents of hydroxyl group and alkyl group with easily removal from body are the follow: several carbon atoms of hydroxy group.

In order to transport to each targeted organ and/or tissue and to effectively generate each targeting effect, pharmaceutically permissive carrier materials are utilized.

For example, pharmaceutically and/or biologically permissible carrier materials are the follow: polyoxyalkylene-alkyl ether, polyoxyethylene sorbitan fatty acid ester, polyvinylpyrrolidone, hydrocarbon, paraffin, alcohol, polyvalent alcohol, alcohol ester, polyalcohol ester, fatty acid and metal salts of fatty acid, artificially produced liposome. Those combinations are also used by a way of mixture, homogeneous diffusion and/or dispersion.

In addition, when vaccine precursor, vaccine, antibody (including idiotype antibody), neutralizing antibody or antitoxin, and vaccine precursor, vaccine, antibody, neutralizing antibody or antitoxin produced by the idiotype antibody mentioned in this invention are used as combined substances with the pharmaceutically permissible carrier materials, those can be applied in various known usages such as milky lotions, suspensions or solutions according to the objective. Also, it is accepted to add solvent-supporting agents, isotonic-adjusting agents, pH adjusters, deodorants, antiseptics or odorants in the compounds mentioned in this invention.

As a method of extracting antigenic substance from an infected cell and/or a cancer cell, for example, it is accepted to be extracted by washing with physiological saline and/or with Triton detergent. And, a combination of manipulation with an ultrasonic wave and frozen processing as a conventional method of cellular destruction is also available. Antibody titer can be enhanced by adding an adjuvant such as $Al(OH)_3$ after treating antigen-included solution. The solution was centrifuged after an inactivation with heating, formaldehyde and/or ultraviolet irradiation.

An additional inactivation of vaccine is accepted to utilize a typical and fundamental processing which has been published (ref. [Provost, P. J., Proc. Soc. Exp. Biol. Med. 160:213 (1979); Provost, P. J., J. Med. Virol. 19:23 (1986)]). Additional inactivation of each targeted extract is the follow: heating, pH modification, irradiation and treatment with an organic solvent such as formalin or paraformaldehyde. However, it is obvious that an extract alone without an additional inactivation can be utilized.

ICOM (immunostimulating complex) which is embedded small granule with an identified chemical structure is also possible to enhance an antigenic property of antibody mentioned in this invention.

As a method of extracting antigenic substance from an infected cell and/or a cancer cell, for example, it is accepted to be extracted by washing with physiological saline and/or with Triton detergent. And, a combination of manipulation with an ultrasonic wave and frozen processing as a conventional method of cellular destruction is also available.

Antigen-included solution which was obtained by a centrifuged separation is used as original antigen. A solution with an additional inactivation with heating, formaldehyde and/or ultraviolet irradiation is also used as an antigen. Then, it is accepted to produce vaccine of which is added a stabilizing agent demonstrated in the following table 1.

TABLE 1

| | |
|---|---|
| Lactose | 2.5% (w/v) |
| Glucose | 2.5% (w/v) |
| Human Albumin | 0.2% (w/v) |
| Gelatin | 0.3% (w/v) |
| Sodium Chloride | 8.0 g |
| Sodium Phosphate (dibasic) | 1.15 g |
| Sodium Phosphate (monobasic) | 0.2 g |

TABLE 1-continued

| Potassium Phosphate | 0.2 g |
| Distilled Water | 1 liter |
| pH | 7.2 |

Also, additional and/or supplemental inactivation of the extract is performed by heating, pH modification, irradiation or a processing with an organic solvent such as formalin or paraformaldehyde after washing sediments of culture medium which includes fragmented components of extincted each cell or bacteria When an extract is treated with formaldehyde, a desirable suspension concentration is between 0.001-0.05 (v/v) %. When an extract is inactivated by ultraviolet irradiation, a desirable range is between $5.0 \blacksquare 10$ $J/m^2$-$5.4 \blacksquare 10^4 J/m^2$ at 356 nm. However, it is better that the above additional inactivation does not apply unless it is needed. A desirable temperature when formaldehyde or ultraviolet irradiation is applied is maintained below 4° C. At any cases, an increased degree of heating, formaldehyde or ultraviolet irradiation markedly changed a titter and/or specificity. For example, a titer of immunoglobulin examined by agar-gel became less than 1/100. Although an original extract alone has been generated an absorption of antigen particle and a clustering of their efficiencies as shown in this invention, it is available to enhance a antibody titer by adding a surfactants such as Twin 80.

Moreover, a property as an adjuvant or carrier is able to be enhanced by an absorption of an inactivated extract with aluminum hydroxide or by a precipitation in aluminum hydroxide. For example, as a first step, sulfuric-acid potassium aluminum is added into a bulk solution which is treated with Yoshixol or which is inactivated by formalin. Then, sediment of inactivated extract is produced in aluminum hydroxide. Final sediment is produced by an addition of sodium hydroxide. After removing formaldehyde and residual salt from a suspension, it is accepted that the residue is replaced into physiological saline.

In addition, a targeted substance is extracted organic-chemically after washing sediment of culture medium with which has an extincted bacteria or cells mentioned above. This is a similar way of conventionally extracting vaccine or antigen. For example, extraction is performed by adding mixture with a bubble- or form-removing agent such as chloroform and isoamylalchol. Then, an extracted solution is flowed DEAE Sephadex gel with 0.1 N hydrochloric acid into a column of which has prepared with 20 mM phosphate buffer solution (pH 7.5), sodium chloride solution of 2 g/liter with 2% formalin and 1M sodium chloride solution. In order to make an equilibrium of a column and to perform a chromatography, pH and concentration of osmotic pressure is adjusted by flowing a phosphate buffer solution of pH 7.5 (20 mM phosphoric acid and 0.1% Twin 80) so that a flowed sample is adjusted an osmotic pressure concentration within a range of 280 mOsm. Then, an infusion rate of a phosphate buffer solution of pH 7.5 (20 mM phosphoric and 0.1% Twin 80) is set on 45 cm/h. An antigenic substance is isolated as a soluble one by this manipulation. A condensation of antibody fraction is obtained by gel-filtration column by an identical condition mentioned above. A final liquid volume after the rinse is adjusted to 2.5 liter. A refined and collected sample is obtained by filtering a condensed antibody fraction through a membrane (Durapore) with a pore size of 0.2 micrometer.

Moreover, as an another gel-filtration, a final processing of gel-filtration chromatography is performed by a negative ion exchange chromatography. An example is a column (K215/100; Pharmacia LTD) which is composited by 26.5 liter of Sepharose 6BCL. A whole system of column apparatus, pipeline and detector is sterilized by solution of 2% formalin and 2% sodium chloride with a flow rate of 1.7 liter/h. Then, a column is rinsed and balanced by pH 7.5 phosphate buffer solution (20 mM phosphoric acid and 0.1% Twin 80) with a flow rate of 2.7 liter/h for 48 hours. After a condensed antigenic substance is added gravitationally into a column, a filtration is performed at a flow rate of 2.7 liter/h with pH 7.5 phosphate buffer solution (20 mM phosphoric acid and 0.1% Twin 80). Then, a refined sample is collected.

As a solvent for extraction, it is available to use a halogenated C1-C6 alkane such as metylenechloride and tetrachloroethane as well as chloroform. In addition, a negative ion exchanger matrix, which is used in an extraction processing due to an ion exchanger chromatography, is not qualified here. There are following examples: DEAE cellulose, DEAE agarose, DEAE biogel, DEAE dextrane, DEAE Sephadex, DEAE Sepharose, aminohexyl Sepharose, ECTEOLA cellulose, TEAE cellulose, QAE cellulose, mono-Q or benzyldiethylaminorthyl cellulose.

The following substances mentioned in this invention are able to utilize themselves alone to achieving the objective mentioned above: vaccine precursor, vaccine, antibody, neutralizing antibody, antitoxin or idiotype antibody and, its vaccine, antibody, neutralizing antibody or antitoxin produced by the idiotype antibody. Those are available to utilize together with acid addition salts, emulsifiers, ester agents or polymerization agents, if their effects, selectivity and/or specificity are not altered drastically by the above combination. The following examples are representative: pharmaceutically permissible non-toxic acid addition salts, inorganic acids such as hydrochloric acid, hydrobromic acid, phosphoric acid or sulfuric acid and organic acids such as acetic acid, citric acid, tartaric acid, lactic acid, succinic acid, fumaric acid, maleic acid or methasulfonic acid.

When vaccine precursor, vaccine, antibody, neutralizing antibody, antitoxin or idiotype antibody which is produced by antigenic substance inductor and, vaccine, antibody, neutralizing antibody or antitoxin produced by its idiotype antibody shown in this invention is used as antibacterial antibody, antiviral antibody, anti-tumor (anticancer) antibody or anti-protozoa (malaria, spirochaeta et. al) antibody, accelerator of immuno-reaction or controller of immuno-reaction, it is accepted to be administered as a single agent or a combined agent with the permissible carrier materials for a drug. When a pain may be induced by subcutaneous injection, a local anesthetic such as xylocaine may be added into an injection solution. However, its method is not limited into an example mentioned in this invention. These compositions on drug delivery depend on routes and/or planning of administration.

When vaccine precursor, vaccine, antibody, neutralizing antibody, antitoxin or idiotype antibody which is produced by antigenic substance inductor and, vaccine, antibody, neutralizing antibody, antitoxin, antibacterial antibody, antiviral antibody, anti-tumor (anticancer) antibody or anti-protozoa (malaria, spirochaeta et. al) antibody produced by its idiotype antibody, which is shown in this invention, are used by oral route as drug such as antibacterial agent, antiviral agent, anti-tumor (anticancer) agent, anti-protozoa agent (malaria, spirochaeta et. al), accelerator of immuno-reaction or controller of immuno-reaction, the following types are available: tablets, capsules, powder materials, granular agents and liquid agents. When the compounds are administered through the non-oral route, those are used in a form of disinfected fluid. When the compounds are used as a form mentioned above, non-toxic carrier materials include in a solid or liquid composition As an example of solid carriers, capsules made by usual gelatin is used utilized. Moreover, effective ingredients are also utilized with supplemental composites or by tabulating, granulating and/or powder packaging without supplemental composites. The following composites are used as the excipients; gelatin, lactose, sugars such as glucose, cone, wheat, rice, starches such as corn starch, fatty acids such as stearic acid, fat bases such as calcium stearic acid and magnesium stearic acid, talc, vegetable oil, alcohol such as stearylalcohol and benzyl alcohol, gum, polyethylene alkylene glycol and so on.

These composites of capsule, tablet, granule and powder are generally between 0.1-80 weight % and contains effective ingredient of 0.1-60 weight %. Liquid carriers such as water, physiological saline, sugar solution, dextrose solution, ethylene glycol, propylene glycol, glycols such as polyethylene glycol, polyoxyethylene sorbitan monoolate are desirable.

When it is administered non-orally by intramuscular injection, intravenous injection or hypodermic injection, the compounds provided in this invention are used as the germ-free solution which is added other solutes such as minerals or glucose in order to make the isotonic solution. Appropriate solvents for an injection represent sterilizing water, solution of lidocaine hydrochloride (for intramuscular injection), physiological saline, glucose solution, various intravenous injection solutions, electrolyte solution (for intravenous injection) and so on. When those solutions are used for the injection, usual dosage is between 0.01-20 weight %. A desirable range is between at 0.05-5 weight %.

In the case of liquids for oral administration, it is better to use as suspension or syrup with 0.01-20 weight %. A carrier of these liquids is watery excipient such as perfume, syrup and micelle which are available for pharmaceutically manufacturing.

The chemical compound which is used and investigated in this invention is not particularly limited. But, as one of a concrete and representative compound which shows reasonable biological effect and which is easily synthesized chemically because of the simple chemical structure, we synthesized 4,4-dimethyl-6-methylene-2-cyclohexen-1-one (this compound is termed as Yoshixol) which is the compound that all of substituent R3, R4, R5 and R6 shown in chemical formula (3-a) are substituted by hydrogen atom. And, except for a special excuse, representative experiments are demonstrated effectiveness of this invention by using this Yoshixol.

BRIEF DESCRIPTION OF THE DRAWINGS

FIG. 1 is a graph which is evaluated a survival rate (mortality) of murine leukemia L1210 as an example of effect of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.

FIG. 5 show an investigated morphological-aspect of murine melanoma cell B16 before and after treatment with antigen structure inductor mentioned in this invention.

EMBODIMENTS OF THE INVENTION

Murine leukemic cells L-1210 (Cancer research institute, Tokyo) was incubated with 2 ml of culture medium (Minimum Essential Medium, Gibco Co.) including bovine fetus serum (Dai-Nipon Pharmace. Co.) at a temperature of 37° C. and 5% $CO_2$ for 30 hours in the incubator. When a number of cells becomes to around $1\times10^6$/ml, cell death is induced by an addition of 4 µl of 2M Yoshixol in ethanol. As a result, a determination of cell viability due to an uptake of methylene blue showed a survival cell of $5\times10^4$ at 2 hours after Yoshixol, closely zero level after 20 hours and zero after 30 hours. After confirming extinction of cells in culture medium, the culture medium of which contains extincted cells was centrifuged at 3,000 cycles/min for 5 minutes so that it's supernant was removed. After adding physiological saline of 0.9 cc into the sedimented component and stirring, a centrifuging separation was performed at 1,000 cycles/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. This filtered solution was injected intraperitoneally at a range of 0.2 cc/mice into CDF-1 strain of male mice (Charles-River Co, Saitama). Control group was treated with a same amount of cell free culture medium. On 31 days after the injection of the filtered solution, 0.3 cc of culture medium ($1\times10^6$ cells/ml) was injected intraperitoneally in each group. Then, survival time of the experimental leukemia was investigated. Subsequently, as shown in FIG. 1, all mice in control group were dead within 8 days after transplantation of cells. In contrast, mice which were treated the filtered solution became to start death on 12 days after the transplantation. Longest survived period was prolonged to 14 days after the transplantation. This result indicates that by a production of antibody as antigen due to residual substance which cell has been destroyed by Yoshixol, it is possible to induce to prolong a survival period of mice in leukemia.

Figure 2A:
FIG. 2a is an electron microscopic aspect of murine leukemia L1210 before treatment with antigenic substance inductor which is mentioned in this invention.
Figure 2B:
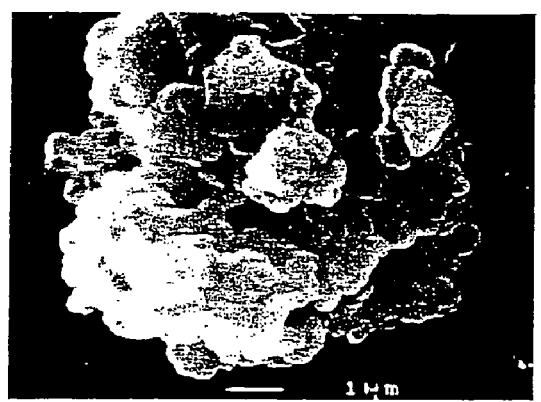
FIG. 2b is an extincted aspect of mouse leukemia L1210 after treatment with antigenic substance inductor. A fine small particle with components of membranes such as proteoglycans is demonstrated.

Morphological changes appeared after treatment with Yoshixol on murine leukemic cells were investigated by scanning electron microscopy (Nihon Densi Co. JSM-6000F). In non-treated (control) group, cultured cells have an irregular pattern such as doughnut-like shape with a central pore of which seems to be a nose of pig, sponge-like structure and spikes. It seems to be an aspect of "weird" (FIG. 2-a); In the contrast, in treated group of which is added 10 µl of Yoshixol into the cultured medium, there were a various patterns of destroyed cells. An appearance of adhesion and aggregation between cells did not find so that a morphological aspect is identical to apoptosis or natural cell death (FIG. 2-b). Thus, these findings suggest that a particle of fragmented cellular component (10-100 nm) such as proteoglycan acts as antigen resulting in higher phagocytosis of macrophages and lymphocytes. Those fragmented particles are involved in a physiological immune surveillance mechanism in vivo.

On an evaluation of survival period of mice mentioned above, a pathological examination of light-microscopy was performed at a timing of the death. An observation was done after being stained by HE. A section of heart, liver, kidney, lung, spleen and intestine has been embed by paraffin and fixed by 10% formaldehyde solution. In non-treated group, an invasion of leukemic cells was found markedly on each organ. Additional histological findings showed portal dilation and stagnation and destroy of vascular wall in liver, and destroy of alveoli and nodule formation from vessels in lung. Also, bloody ascites was found characteristically. On the other hand, in the treated group with the immunization, a histological aspect was similar to that in non-treated group, however, a degree of each characteristic finding was less than that in non-treated group. Except for a bloody ascites, a qualitative finding is similar between both groups although a histological aspect has been observed at postmortem. This result suggests that at least treatment with vaccination mentioned in this invention is related to biological mechanism of inhibiting to induce a blood ascites (possibly, damage of vascular wall) due to transplanted leukemic cells.

Figure 3:
FIG. 3 is a graph of immuno-electrophoresis which demonstrates to induce a new production of antibody in rabbit serum against murine leukemia L1210 as an example of effect of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.
Figure 4A:
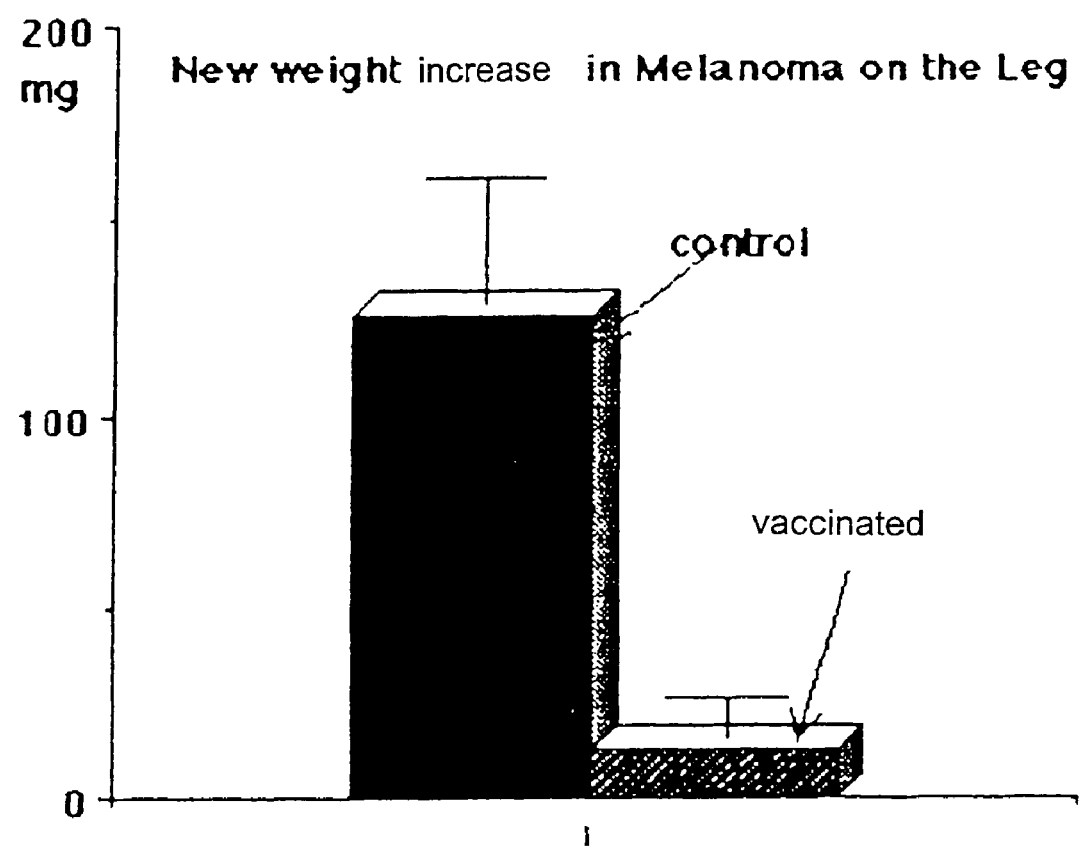
FIG. 4 is the graph which is evaluated changes in tumor weight of melanoma cells B16 implanted to foot-pat and a number of colony formation in lung as an example of effect of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.
Figure 4B:
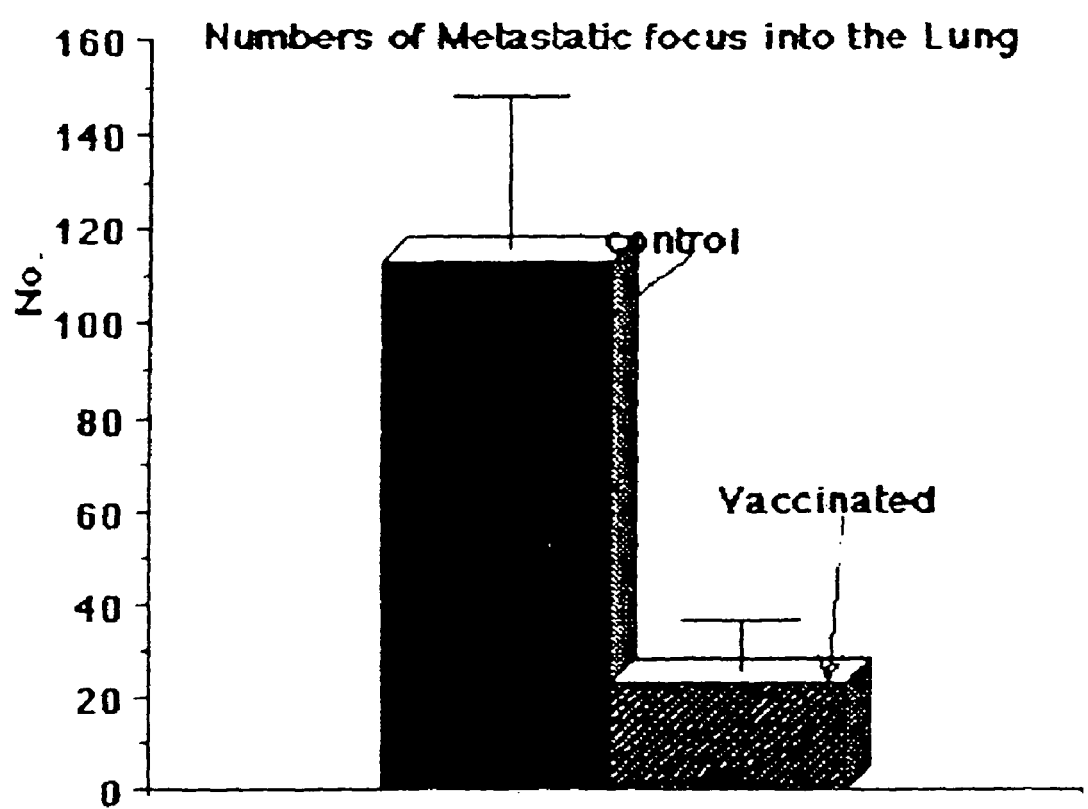

Murine leukemic cells L-1210 purchased from Cancer research institute, Tokyo, was incubated with 2 ml of culture medium (Minimum Essential Medium, Gibco Co.) including bovine fetus serum (Dai-Nipon Pharmace. Co.) at a temperature of 37° C. and 5% $CO_2$ for 30 hours in the incubator. When a number of cells become to around $1\times10^6$/ml, cell death is induced by an addition of 4 µl of 2M Yoshixol in ethanol. As a result, a determination of cell viability due to an uptake of methylene blue showed a survival cell of $5\times10^4$/ml at 2 hours after Yoshixol, closely zero level after 20 hours and zero after 30 hours. After confirming extinction of cells in culture medium, the culture medium including extincted cells was centrifuged at 3,000 cycles/min for 5 minutes so that its supernant was removed. After adding physiological saline of 0.9 cc into the sedimented component and stirring, a centrifuging separation was performed at 1,000 cycles/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. This filtered solution of 1 cc was injected intravenously in a rabbit. One month after the injection, the rabbit was sacrificed by bleeding under Nembutal anesthesia. Serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against mice leukemic cells. Subsequently, it was confirmed to be formed a new band of immunoglobulin as shown in FIG. 3.

In addition, rabbit serum as the control which was shown in this example was produced by the following. In a Japanese white rabbit which was born from a parent as same as a rabbit which was used in the above example, 10 µl/Kg of 2 M Yoshixol with ethanol was injected intravenously for 3 min via a ear vein. Solution of Yoshixol was mixed with culture medium of 5 ml. The medium was filtered through miliporefilter of cellulose acetate (pore size, 0.45 µm). Any abnormal sign did not find immediately after the injection through one month. A rabbit was sacrificed under Nembutal anesthesia one month after the injection. Blood was removed. Then, serum was obtained after removal of cell components by a centrifugation.

Moreover, the immune electrophoresis which was demonstrated in this invention was performed the following procedure. However, this invention is not restricted by the investigative procedure demonstrated here. Firstly, 1% agar-sol was made by heating and melting 1 g of agar-agar (Wako Pure Chemical LTD.) with 100 ml of 0.03 M Veronal buffer solution. Veronal buffering solution (pH 8.6) was prepared by a mixture of 5,5-diethylbarbituric acid (Wako Pure Chemical LTD.) and sodium nitride (Wako Pure Chemical LTD.). As a procedure, firstly, agar-plate was made on a glass plate (10 cm×10 cm) cleared with ethanol gauze after pouring agar-sol. Original core point and a groove which are added each serum is designed on a paper with scale. The paper was set on an agar-gel plate after being harden the agar-sol. Then, a part of agar-gel was removed in order to obtain a holding space (well) for sample. Thereafter, a 4 ul sample of rabbit serum added bromphenol blue (Wako Pure Chemical LTD.) was replaced into the well. And, electrophoresis was performed by use of an electrophoretic apparatus (power supply ATT0-Power Station 1000VC) with a constant current of 2-3 mA for about 18 hours after replacing the gel in the chamber following a method of Ouchterlony. Then, after taking the gel off from the chamber, a part of gel with a marker previously as a groove was removed. Into this groove, goat serum against rabbit of 58 mg/ml was added. Then, it was reacted at a room temperature for an overnight. The gel was preserved in the humidifier box in order to prevent drying. After the preparation, the gel was dipped in a physiological saline for one day. In order to remove dust and contamination, the gel was dipped in distilled water. The gel was stained by CBB staining solution (Wako Pure Chemical LTD.) in order to investigate clearly. Then, the gel was rinsed and/or discolored by distilled water. A plate of the gel was recorded on the videotape to digitalize, analyze and illustrate. Criteria of position, contrast, radius and/or symmetry of precipitin line were used to judge a production of immunoglobulin. Generally, when amount of a newly produced antibody (or sample serum) is large, position of precipitin line is shifted toward the antibody in a groove and contrast of precipitin line is reduced. When an amount of a newly produced antibody is less, position of precipitin line is nearer to an axis of the well and contrast of precipitin line toward the well is reduced. Furthermore, when a molecular weight is smaller, position of precipitin line is shifted toward the antibody in a groove and radius of precipitin line becomes larger. In contrast, when a molecular weight is larger, a radius of precipitin line becomes smaller. When a newly produced antibody is homogenous, precipitin line is symmetrical. And, when a newly produced antibody is heterogeneous, precipitin line is asymmetrical.

Murine melanoma cells (B16; purchased from Riken Cell Bank) was incubated with 2 ml of culture medium (Minimum Essential Medium, Gibco Co.) including bovine fetus serum (Dai-Nipon Pharmace. Co.) at a temperature of 37 ■ ■ and 5% $CO_2$ for 30 hours in the incubator. When a number of cell becomes to around $2\times10^5$/ml, cell death is induced by an addition of 4 μl of 2M Yoshixol in ethanol. Then, the culture medium with extincted cells was centrifuged at 3,000 cycles/min for 5 minutes so that its supernant was removed. After adding physiological saline of 0.9 cc into the sedimented component and stirring, a centrifuging separation was performed at 1,000 cycles/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. This filtered solution of 0.2 cc was injected intraperitoneally in C57/BL mice (female, 6 weeks after the birth, purchased from Nihon SLC Co.). Thirty days after the injection of the filtered solution, 0.3 cc of mice melanoma cells ($2\times10^5$/ml) was transplanted on a foot-pat of mice in vaccinated (treated) group and in control (non-treated) group. Then, local growth and metastasis to lung of melanoma cells (B16) were investigated. Subsequently, as a result, a net weight of distal leg from knee joint in the control mice was 120 mg on an average at 45 days after the cell transplantation. However, a net weight of distal leg from knee joint in the treated mice with the filtered solution was 11 mg on an average at 45 days after the cell transplantation. In addition, on a pathological investigation of lung metastasis, a pin-point like small focus of metastasis on the lung was more than 122 on an average in the control group and was less than 10 in the treated group. This result shows that a local growth and/or metastasis of melanoma cells are inhibited by promoting a new production of antibody in vivo in mice, resulting from using substances of extincted cell by Yoshixol is used as an antigen.

Figure 5A:
FIG. 5a is an aspect of phase-contrasted microscopy without the treatment.
Figure 5B:
FIG. 5b is an aspect of phase-contrasted microscopy with the treatment.
Figure 5C:
FIG. 5c is a scanning electron microscopic aspect.

Morphological changes appeared after treatment with Yoshixol on mice melanoma cells B16 were investigated by scanning electron microscopy (Nihon Densi Co.JSM-6000F) similar to the investigation of leukemic cells. In non-treated group, an aspect of cultured cells is proliferating pattern likely to regular rocky wall, an existence of mitotic cells and a normal intracellular appearance. An intercellular matrix is filled with extracellular substances (FIG. 5a). In contrast, morphological aspects of cultured cells in treated with 4 ul of Yoshixol showed various irregular appearances such as destroyed structure of cellular membranes and/or organelle, and showed a separation of connection between cells and of various sizes of particles consisted of cellular membranes from cells (FIG. 5b). And, cultured cells in treated group showed various patterns of destruction and did not show an adhesion and/or aggregation between cells. Those indicate a similar morphological aspect to natural cell death or apoptosis (FIG. 5c). These particles of fragmented cellular components (10-100 nm), namely proteoglycans, act on an antigen resulting in phagocytotic effects of macrophages and/or lymphocytes. Thus, those fragmented particles are combined into physiological immune surveillance mechanism in vivo. Subsequently, these morphological aspects suggest that antibody to recognize melanoma cell (B16) in vivo is produced resulting in molecular recognition.

Figure 6:
FIG. 6 is a graph of immuno-electrophoresis which demonstrates to induce a new production of antibody in rabbit serum against murine melanoma cell B16 as an example of effect of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.

Murine melanoma cells (B16; purchased from Riken Cell Bank) was incubated with 2 ml of culture medium (Minimum Essential Medium, Gibco Co.) including bovine fetus serum (Dai-Nipon Pharmace. Co.) at a temperature of 37 ■ ■ and 5% $CO_2$ for 30 hours in the incubator. When a number of cells becomes to around $2\times10^5$/ml, cell death is induced by an addition of 4 ul of 2M Yoshixol in ethanol. After confirming extinction of cells in culture medium, the culture medium with extincted cells was centrifuged at 3,000 cycles/min for 5 minutes. Then, its supernant was removed. After adding physiological saline of 0.9 cc into the sedimented component and stirring, a centrifuging separation was performed at 1,000 cycles/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. This filtered solution of 1 cc was injected intravenously in a rabbit. One month after the injection, the rabbit was sacrificed by bleeding under Nembutal anesthesia so that blood was removed. Serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against murine melanoma cells. Subsequently, it was confirmed to be formed a new band of immunoglobulin as shown in FIG. 6.

Figure 7:
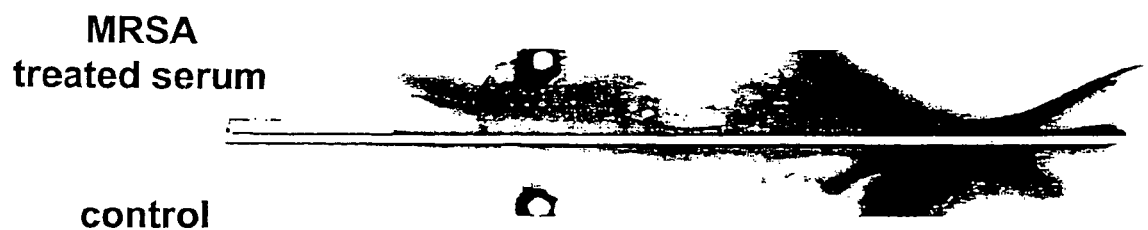
FIG. 7 is a graph of immuno-electrophoresis which demonstrate to induce a new production of antibody in rabbit serum against methicilin resistant *Staphylococcus aureus* as an example of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.

Effect of Yoshixol on MRSA was investigated by using the original strain (stock no. SCK18) which was isolated from sepsis patient and which was confirmed to cause severe circulatory shock in experimental animals such as mouse, rat, rabbit and dog. Culture medium was used a brain-heart infusion agar (Nisui Pharma. Co.). In treated group with ethanol solution of 2 M Yoshixol (concentration of 10 ul/ml broth) at a condition of $7.6 \times 10^8$ and 37 ■, ■ CFU was zero at 24 hours after the incubation. This cultured medium of 0.1 ml on a share filled with heart infusion agar medium (Eiken Kagaku Co.) was additionally sprayed and incubated at 37 ■ ■ for 48 hours. However, no colony growth was found. The culture medium of which contains extincted bacterial component of 5 cc mentioned above was centrifuged at 1,000 cycles/min for 5 minutes. Then, its supernant of 2.5 cc was removed. After adding physiological saline of 2.5 cc into the remained solution of 2.5 cc and a mixture, a centrifuging separation was performed at 1,000 cycle/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. As a result, a test solution of 3 cc was obtained. This filtered solution of 1.5 cc was injected intravenously in a rabbit. One month after the injection, the rabbit was sacrificed by bleeding under Nembutal anesthesia so that the serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against MRSA. Subsequently, it was confirmed to be formed a new band of immunoglobulin as shown in FIG. 7. This result indicates that Yoshixol is capable to produce a beneficial antibody against MRSA, of which an acquired drug-resistance against antibiotics as a major grain-positive bacteria.

Figure 8:
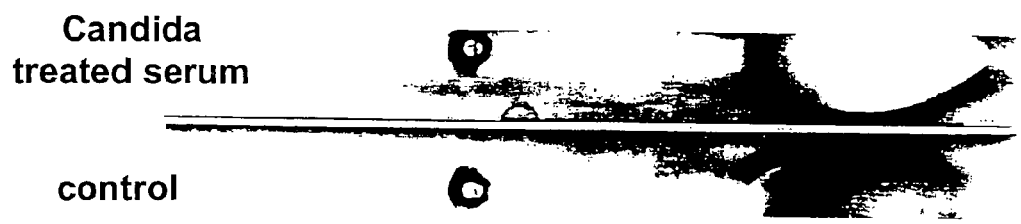
FIG. 8 is a graph of immuno-electrophoresis which demonstrates to induce a new production of antibody in rabbit serum against *Candida albicans* as an example of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.

In order to investigate effect of Yoshixol on *Candida albicans*, it was investigated by using *Candida albicans*. The used medium was Sabouraud broth (5 ml) and number of *Candida albicans* was $5.2 \times 10^6$ CFU/ml. In treated group with ethanol solution of 2 M Yoshixol (concentration of 10 ul/ml broth) at a condition of $10^8$ and 37 ■, ■ CFU was zero at one and 3 hours after the incubation. This cultured medium of 0.1 ml on a share filled with heart infusion agar medium (Eiken Kagaku Co.) was additionally sprayed and incubated at 37 ■ ■ for 48 hours. However, no colony growth was found. The culture medium of which contains extincted bacterial component of 5 cc mentioned above was centrifuged at 1,000 cycles/min for 5 minutes. Then, its supernant of 2.5 cc was removed. After adding physiological saline of 2.5 cc into the remained solution of 2.5 cc and a mixture, a centrifuging separation was performed at 1,000 cycle/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. As a result, a test solution of 3 cc was obtained. This filtered solution of 1.5 cc was injected intravenously in a rabbit. One month after the injection, the rabbit was sacrificed by bleeding under Nembutal anesthesia so that the serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against *Candida albicans*. Subsequently, it was confirmed to be formed a new band of immunoglobulin as shown in FIG. 8. This result indicates that Yoshixol is capable to produce a beneficial antibody against *Candida albicans* by a complex substance, which is obtained after an extinction of *Candida albicans* by Yoshixol.

Figure 9:
FIG. 9 is a graph of immuno-electrophoresis which demonstrates to induce a new production of antibody in rabbit serum against *Pseudomonas aureginosa* as an example of effect of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.

Effect of Yoshixol was investigated by using *Pseudomonas aureginosa*. The used medium was heart infusion agar medium (Nisui Pharma Co,). In treated group with ethanol solution of 2 M Yoshixol (concentration of 10 ul/ml broth) at a condition of $10^8$ and 37° C., CFU was zero at one and 3 hours after the incubation. This cultured medium of 0.1 ml on a share filled with heart infusion agar medium (Eiken Kagaku Co.) was additionally sprayed and incubated at 37° C. for 48 hours. However, no colony growth was found. The culture medium of which contains extincted bacterial component of 5 cc mentioned above was centrifuged at 1,000 cycles/min for 5 minutes. Then, its supernant of 2.5 cc was removed. After adding physiological saline of 2.5 cc into the remained solution of 2.5 cc and a mixture, a centrifuging separation was performed at 1,000 cycle/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. As a result, a test solution of 3 cc was obtained. This filtered solution of 1.5 cc was injected intravenously in a rabbit. One month after the injection, the rabbit was sacrificed by bleeding under Nembutal anesthesia so that the serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against *Pseudomonas aureginosa*. Subsequently, it was confirmed to be formed a new band of immunoglobulin as shown in FIG. 9. This result indicates that Yoshixol is capable to produce a beneficial antibody against *Pseudomonas aureginosa* by a complex substance of which is obtained after an extinction of *Pseudomonas aureginosa* by Yoshixol.

Figure 10:
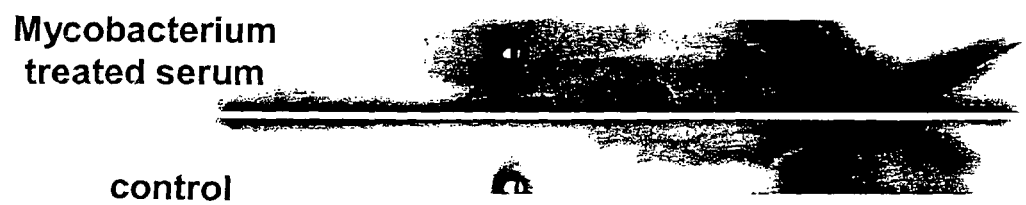
FIG. 10 is a graph of immuno-electrophoresis which demonstrates to induce a new production of antibody in rabbit serum against *Mycobacterium* rapid grower as an example of effect of the following substances: vaccine precursor, vaccine, antibody, neutralizing antibody, antitoxin and idiotype antibody of which is produced by use of antigenic substance inductor in this invention: and anti-idiotype antibody which is produced by its idiotype antibody.
Figure 11A:
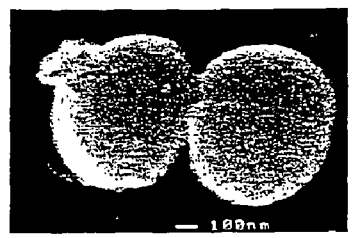
FIG. 11a shows an electron microscopic aspect of methicilin resistant *Staphylococcus aureus* treated with antigenic substance inductor mentioned in this invention. Each of FIGS. 11b, 11c, 11d, and 11e shows an extincted aspect investigated by an electron microscopy on *E. coli, Candida albicans, Pseudomonas aureginosa* and *Mycobacterium* rapid grower, respectively. Each picture demonstrates an appearance of a small particle with membrane components of each bacteria.
Figure 11B:
Figure 11C:
Figure 11D:
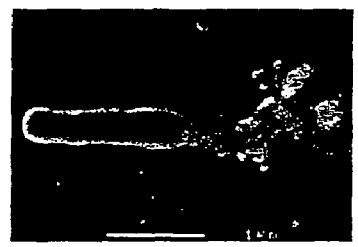
Figure 11E:

Effect of Yoshixol was investigated by using a typical mycobacteria (*Mycobacterium* Rapid Grower). The used medium was heart infusion agar medium (Nisui Pharma. Co,). In treated group with ethanol solution of 2 M Yoshixol (concentration of 10 ul/ml broth) at a condition of $3.3 \times 10^5$ and 37° C., CFU was zero at one and 3 hours after the incubation. This cultured medium of 0.1 ml on a share filled with heart infusion agar medium (Eiken Kagaku Co.) was additionally sprayed and incubated at 37° C. for 72 hours. However, no colony growth was found. The culture medium of which contains extincted bacterial component of 5 cc mentioned above was centrifuged at 1,000 cycles/min for 5 minutes. Then, its supernant of 2.5 cc was removed. After adding physiological saline of 2.5 cc into the remained solution of 2.5 cc and a mixture, a centrifuging separation was performed at 1,000 cycle/min for 5 minutes. This procedure was repeated twice. Then, after adding physiological saline of 0.9 cc in the rinsed residue of sediment and stirring, the mixture solution was filtered by miripore-filter of cellulose acetate with 0.45 micrometer pore size. As a result, a test solution of 3 cc was obtained. This filtered solution of 1.5 cc was injected intravenously in a rabbit. One month after the injection, the rabbit was sacrificed by bleeding under Nembutal anesthesia so that the serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against atypical acid-fast bacterium. Subsequently, it was confirmed to be formed a new band of immunoglobulin as shown in FIG. 10. This result indicates that antigenic substance inductor is capable to produce a beneficial antibody against atypical acid-fast bacterium by a complex substance of which is obtained after an extinction of atypical acid-fast bacterium by Yoshixol.

Such effects of Yoshixol on microorganism showed an interest finding concerning on a morphological change in death process. Various aspects of scanning electron microscopy (SEM) were found: one of the aspect was that cluster formation of MRSA was disappeared and separated individually, resulting in small granule formation of 10-50 nm which was taken a similar pattern to eruption (FIG. 11-a). Another example of a morphological aspect as a possible and final one was a concentric circular pattern of small granule likely a firework. Similar aspects were found by a transmission electron microscopy. An investigation of *E. coli* on SEM showed a production of many round-shape particles (10-50 nm) on the surface. A smooth surface was disappeared and a formation of prominence-like swelling was appeared (FIG. 11-b). In this case, identically to MRSA, a clustering formation of bacteria was disappeared resulting in a small fragmentation as a final morphological appearance. Similar morphological aspects were found on acid-fast bacteria (FIG. 11-c) and *Candida albicans* (FIG. 11-d). In addition, a final aspect of dispersed and/or swelled cellular structure on *Pseudomonas aureginosa* was found (FIG. 11-e). A characteristic mechanism of Yoshixol with antibacterial and/or bactericidal action are to block an adhesion between each bacteria and to produce granular particles of bacterial components, which depend on molecular components related in the morphogenesis of each microorganism, resulting from a process of morphological changes such as eruption, explosion and/or ballooning structure. This extinct mechanism is different from a mechanism of conventional antibacterial and/or bactericidal agents, of which cause degeneration, necrosis and aggregation. These morphological findings indicate that those disruptive particles become to be transferred into specific macromolecules with species difference of microorganism, resulting in specific antigen.

Figure 12A:
FIG. 12a is a transmission electron microscopic aspect of extincted methicilin resistant *Staphylococcus aureus* after treatment with antigenic substance inductor mentioned in this invention.
Figure 12B:
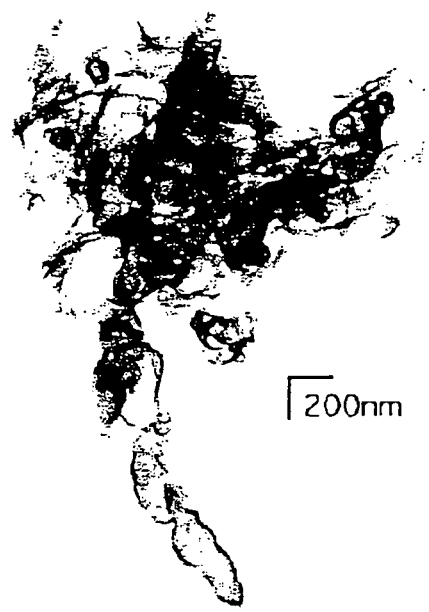
FIG. 12b is a transmission electron microscopic aspect of extincted *E. coli*. A fine small particle with membrane components such as peptidoglycans or proteoglycans is demonstrated.

Furthermore, when electron microscopic investigation was performed on disruptive final structure of each microorganism, a morphological aspect was identical to peptidoglycans. A similar appearance of transmission electron microscopic investigation was found between *Staphylococcus aureus* (FIG. 12-a) and *Pseudomonas aureginosa* (FIG. 12-b). This finding suggests that peptidoglycans consisting of cell wall of microorganism, which is separated by treatment with Yoshixol, act as effective and specific antigen.

Figure 13:
FIG. 13 is a graph of immuno-electrophoresis which demonstrates to induce a new production of antibody in rabbit serum against a mixed solution with chondroitin sulfate, fibrinogen, actin and insulin as an example of effect of the following substances: vaccine precursor, vaccine, antibody, neutralizing antibody, antitoxin and idiotype antibody which is produced by use of antigenic substance inductor in this invention: and anti-idiotype antibody which is produced by its idiotype antibody.

A combination solution of chondroitin sulfuric acid (5 g, Taiyo-Suisan Ltd., Japan), actin (1 mg, Sigma, USA), human fibrinogen (0.5 mg, Diagnostica Stago, France) and insulin (1.6 mg, Nova, Cophenhagen) was made with 1 ml of physiological saline. After adding Yoshixol (10 μl) into the solution, this solution was filtered. The filtered solution by miripore-filter of cellulose acetate with 0.45 micrometer pore size was injected intravenously in a rabbit. One month after the injection, the rabbit was sacrificed by bleeding under Nembutal anesthesia so that the serum was obtained after removal of cell components by a centrifugation. This serum was examined by an agar-gel diffusion of rabbit serum antibody against goat serum (Jackson ImmunoResearch Lab, Pa., USA) in order to define whether this serum has been produced an antibody (immunoglobulin) against complex components of chondroitin sulfate, actin, human fibrinogen and insulin. Subsequently, it was confirmed to be formed a new band of immunoglobulin as shown in FIG. 13. This result indicates that a treatment with Yoshixol on chondroitin and/or protein complex is capable to produce a beneficial antibody against chondroitin and/or protein which has not an antigenic property itself. In addition, this finding suggests that an antigenic substance inductor such as Yoshixol has a potency of hapten.

On the above mentioned, examples of investigations in this invention has been demonstrated. However, it is obvious that this invention is not restricted by examples of investigations mentioned above and is able to be applied and modified within a range of innovation of this invention when it is needed.

A mechanism of effects and actions in this invention was explained by using Yoshixol as a representative example of inhibitory or blocking agents of molecular generating and/or inducing functions. This has been published in the international publication No. WO96/07403. However, as mentioned above, this invention is not restricted by the investigated preparations demonstrated here.

<Summary of Primary Effect and Mechanism, and Its Significance>

In this invention, a wide-ranged and concrete effects and/or actions related to molecular recognition, generation of function, signal transduction and antigen-antibody reaction was discussed briefly. However, to cite each reference of scientific back-ground is far from the aim of this application so that the following two issues are cited as references of scientifically known events. <ref. 1> by Bern and Levy, Physiology, Sanders Publishing Inc.: <ref. 2> by Alberts, Ray, Lewis, Raff, Roberts and Watson, The Molecular Biology of the CELL, Garland Publishing Inc.:

In an immune system, it is divided into following two pathways. In the humoral antibody response, as the first pathway, a produced antibody circulating into the blood stream causes a specific ligation to an antigen of foreign body of which induced a production of the antibody. When an antibody binds with the antigen, phagocyte becomes to easily capture the antigen and, proteins such as complements in blood become to be activated by its antibody, resulting in a promotion of destroying the antigen. As the second pathway, cell-mediated immune response is a response to produce particular cells. Those cells can react with antigen of a foreign body on the surface of host cells. These cells act against an antigen, resulting from killing host cells when antigen is an infectious virus and from inducing another cells such as phagocytes with a potency of destroying antigen. Moreover, it is a fundamental knowledge that T cell relates to cellular immune response and B cell produce an antibody. B cell produces an antibody-molecule with different antigen-binding site between each clone. Firstly, cells bind antibody-molecule to the cellular membrane. This molecule on the membrane acts as surface receptor of the cells against an antigen. An antigen links to this binding site so that B cells are activated. Then, a proliferation of B cells occurs. These cells become to produce a lot of antibody, resulting in a release into the circulatory blood.

From the fact which a three-dimensional structure (conformation) of protein molecule such as antibody is determined by only an amino acid sequence, its conformation recovers to be able to bind with an antigen although a denatured (unfolding) antibody-molecule has not an antigenic potency. When antigen links with this surface receptor of cells, cells are activated resulting in a proliferation and growth. Thus, a foreign body antigen has been already provided for a correlative receptor with specificity against the antigen, resulting in selective stimulation of cells, of which are into a reactive stage. This is the reason why antigenic specificity appears in an immune response and is a fundamental basis of an immune surveillance mechanism. Moreover, it is thought that most macromolecules including all of proteins and polysaccharides have a potency to become antigen.

Antigen determinant is a binding site with antigen-binding site of receptor of antibody-molecule or lymphocytes, which exists on the surface of antigen. Hapten is a molecule of which is not able to induce an immune response by itself. However, it can produce a specific ligand with the receptor of antibody or lymphocyte. Hapten becomes an antigen when it is linked with a carrier of adequate macromolecules. Hapten of which have been used generally in immunological experiments is dinitrophenol (DNP). Usually, DNP is utilized by binding with proteins as an antigen. This invention indicated that a family of Yoshixol demonstrated in examples in this invention is a molecule of which becomes to be hapten.

Any types of antibodies have two characters; one is a membrane-binding type which acts as a specific surface receptor of cells against antigen and another is to exist as a water soluble secretary type. IgM and IgD are major parts of antibody on the surface of B cells of which are in a resting stage.

A binding between antigen and antibody is reversible similar to a binding between substrate and enzyme. This binding is a summation of many non-covalent binds with relatively week force including in hydrophobic bind, hydrogen bind, van der Waals force and ion interaction. These week forces act efficiently when a position of atoms within antigen-molecule is fitted to the homologous folding on the surface of antibody resulting from sufficiently closing toward antibody (It has been understood as a relationship between key and keyhole). However, this invention demonstrated that this concept is accepted even by a logical basis of quantum thermodynamics of molecule. Moreover, antiserum against an antigen generally produces a cross-link with antigen. Antiserum is a complex material consisting of various antibodies of which are able to react with various antigen determinants (polyclonal antibody). If a combination of antigen and antibody is an adequate binding affinity and a formation of higher aggregation, a size of antigen-antibody complex is determined by a relative molar concentration between antigen and antibody. Producing and/or manufacturing processes of vaccines and antibodies mentioned in this invention are reasonable and appropriate on a basis of chemical property of Yoshixol of which was used as a representative molecule in examples of this invention.

The successful result of immuno-chemistry at the present time is that an idiotype antibody is a fundamental basis of immune network. Antibody itself plays an important role of controlling immuno-response as well as biological defense against infections. Thus, when antibody is released against an antigen and is linked with the antigen, a receptor on B cells becomes to be stimulated because of loss of binding with antigen. Then, an immune response is ceased. This system is a simple feed-back inhibitory mechanism. In addition, antibody consists of a part of immunological network and plays more complicated roles on immunological modulation and/or regulation. This system is an acquired biological defense and/or survival mechanism. On the basis of this network system, specificity and/or diversity of species is preserved. Also, a significance of this invention is to utilize diversity on this evolutionary event.

In addition, antibody itself has an antigenic property so that there is a possible to produce an antibody which is recognized a part of C.V region of immunoglobulin chain as a antigen determinant. When antigen-binding site becomes to be such antigen determinant namely on the V region of L.H chain, this antibody is termed as an idiotype antibody. A different antigen-binding site becomes to be a different idiotype antibody so that more than million of antigen-binding sites with animals become to be further more than million of idiotype antibody. Because of a less existence of each idiotype antibody in body, animals do not to become to an immune tolerance. Thus, a response to both T cells and B cells easily occurred.

For example, it is thought that animals which have been immunized by antigen A produces much amount of anti-A antibody so that animals produce antibody against idiotype antibody of anti-A antibody. Following this process, animals produce antibody against anti-idiotype antibody. This reaction continues sequentially. An existence of this immune network mechanism has been proofed by a fact that a major part of antibody produced by an initial response to antigen becomes a same idiotype antibody. Such simple immune response causes to produce antibody of which has a property of specific recognition against idiotype antibody and to activate T cells. Subsequently, an activation of lymphocytes with the idiotype antibody as receptors becomes to be inhibited or promoted.

There are many biological significances which individuals themselves are able to produce own antibody against idiotype antibody. Probably, a number of idiotype antibodies are at least as same as a number of antigen determinants. In other wards, a standard antigen determinant has to recognize one of idiotype antibody at least in own immune system. An antigen determinant of these immune system forms latently a complex network of overall interaction between idiotype antibody and anti-idiotype antibody. In addition, it seems that there is a little of overlap of idiotype antibody between T cells and B cells, each type of lymphocytes is probably related to these kinds of networks. Therefore, it has been recently suggested a concept that immune responses are reflectable vibrations (likely to attenuating oscillation) better than these responses are individual responses to antigen on lymphocytes. This possible immunological concept is identical to the fundamental idea of this invention.

A major component of sequential reaction of protein degradation on such immune response is C3 component of complement. Activation due to such degradation becomes a central reaction of a sequential activating complement. However, a kind of polysaccharides of which exist on a cellular surface of microorganisms preserves C3b-like molecule with such membrane-binding property and avoids to degenerate and/or destroy these substances. It has been known that on sequential reaction of complements, a small fragment of proteins with a biological activity is produced by degradation of various components of proteins. It has been thought that a sequential reaction of this complement is controlled exactly to attack only a near-closed membrane. An inactivation of these active components occurs at least by two processes. Firstly, when a specific blocking protein in blood is activated by protein degradation, an active component becomes to cease a sequential reaction followed by biding and/or fragmenting a specific component of protein. For example, a blocking protein prevents a promoting of a further action by a binding formation with an activated component of C1 complexes. Furthermore, other blocking proteins exist in blood. These proteins lead to inactivate followed by fragmenting Cab. It is reasonable from a fact that if these blocking factors do not exist, C3 complement has to be completely exhausted by positive feed-back mechanism of alternative pathway. Secondly, an activated component in sequential reaction has an unstable component so that this component plays an important role on control of the reaction. These unstable components become rapidly to loss their actions when these do not bind with an adequate component on sequential reaction or with a near-closed membrane, namely concerning on C4 and C3b. Either component becomes an activated one with a short life-span resulting from a sequential and a rapid alteration of its conformation when the component is fragmented. This activated one has a hydrophobic region and a highly reactive side chain of glutamic acid, resulting from a mechanical fragmentation of a specific thioeter ligand in proteins. Subsequently, this glutamic acid immediately forms a covalent binding with proteins or polysaccharides of a near-closed membrane. A half time of this activated one is extremely short (less than 0.1 msec). Therefore, C4 and/or C3b are not able to bind only to a near-closed membrane with a required complement for activation. Thus, it seems that an attack of complement is limited to the surface of microorganism and is not expanded to normal host cells of which are existed nearly. In addition, a fragmentation of thioester between side chains of proteins generates to produce an extreme reactive carbonyl group. This carbonyl group causes a covalent binding with macromolecule so that ester or amido linkages are formed. However, those abilities of proteins disappear within 60 microseconds of a half-life time so that a reactive acceptor site is limited in a membrane nearly close to fragmented and/or activated site of peptide binding. Effects such as examples demonstrated in this invention are reasonable together with the above bio-chemical knowledge and a chemical property of Yoshixol of which was used as a representative one in examples in this invention.

An antigen idiotype antibody, which causes sequential reaction of protein degradation of complement, binds not only with anti-X antibody but with B cells which has an identical surface antibody as a receptor against antigen X. When anti-idiotype antibody binds to a receptor on the surface of B cells, ability of recognition and/or response on B cells against antigen X is inhibited. It has been suggested a possibility that common idiotype antibody concerning to receptors of both B and T cells is corded by a gene fragment which determines V region of H chain on immunoglobulin. However, another possibility is that a receptor of T cells is produced by a gene fragment of which cords VH region of general antibody because of a blend new class of immunoglobulin. It has been suggested that both B cells and T cells, which react with same antigen, become to induce an identical idiotype antibody (antigen determinant which exits on the binding site of antibody) on a surface receptor of the cells. This invention has a higher significance of production and/or manufacture of idiotype antibody followed by applying a family of Yoshixol of which was used as a representative molecule in examples of this invention. That is to smoothly provide idiotype antibody along evolutional diversity without a biogenetic manipulation when the antibody is needed.

When cytotoxic T cell contacts to cells of different species and/or mammalian cells infected by virus, cytotoxic T cell becomes to be an activated effector cells for a few days. Then, these T cells kill the cells of different species and/or mammalian cells by a specific linkage with a triggered cell of the activation. Helper T cells are needed to produce antibody responded to antigen, however, there are many antigens which are able to activate B cells without assistance of T cells. Such T cell independent antigen is a large polymer generally with a repeated structure of same antigen determinant. A recognition of a regulatory T lymphocyte to a targeted cell is an interaction between idiotype antibody and anti-idiotype antibody as a one or reaction pathways. In a case of antibody production of an identical idiotype antibody, two types of T cells are found on a response to antibody. One is to recognize a foreign body antigen and second is a membrane binding idiotype antibody of which acts on the surface of B cells as a receptor. In any cases, another significance of this invention is that production and/or manufacture of idiotype antibody induced by a family of Yoshixol, which was used as a representative molecule in examples of this invention, makes a possible way of a new contribution to define scientifically a complexity of immune networks as one of logistic tools.

The following comments is pointed out although those are repeated; idiotype vaccine has been researched and developed as an ideal one. This concept is that antibody molecule has an own specific molecular structure (conformation and/or topology) of which can be fitted with an antigen determinant so that an immunization of the antibody to animals produces antibody against its determinant site. This antibody is anti-idiotype antibody. Therefore, an excellent linkage occurs between anti-idiotype antibody and antigen binding site (idiotype) of an original antibody. These indicate an existence of common structure (conformation and/or topology) between antigen determinant and anti-idiotype antibody. Thus, anti-idiotype antibody has a possibility to be applied as another antigen. This mention does not indicate to rule out the combination of manipulation and/or preparation of conventional inactivation and/or attenuation. The anti-idiotype antibody is less biohazard for a handling because of antibody molecule. Another reason is to be able to induce a species specificity selectively and combinationaly. Thus, DNA recombination has a possibility to mislead a portion of polysaccharide chain, in spite of identical sequence of peptide region. The idiotype vaccine and/or anti-idiotype vaccine have a characteristic property to be a more natural antibody.

As one of immunological surveillance system, tumor-related antigen is to induce immune response to tumor cells. A temporal existence of this tumor-related antigen appears at an initial stage of development so that this antigen is disappeared in normal development. However, there are several types of abnormal appearances such as ■-fetoprotein of which is appeared again after the disappearance by a formation of tumor, antigen of which is appeared by a formation of tumor originated another tissue from an initial tumor tissue, antigen of which allogenic antigen is induced by a formation of tumor and of which is not preexisted in individual, antigen originated by virus, antigen of which is induced by activation of oncogenes, antigen of which is produced a new antigen with a changed polysaccharide chain of cellular, membrane substances by a abnormal metabolism associated with a formation of tumor and idiotype antigen of surface immunoglobulin in a tumor of B cell groups. In those examples, antigen of which is appeared only in tumor cells, but not in any normal cells, is called as tumor related antigen. However, a little of existences has been identified at the present time. Thus, advanced research activities have been focused at a level of genetic analysis. This invention is utilized anti-tumor or anti-cancer action published in the international patent file (PTC: WO96/07403) related on inhibitory or blocking agents of molecular generating and/or inducing functions. Also, this invention is utilized a mechanism of action of which is able to induce a destroyed microstructure dependent on morphological and functional specificity of tumor cells and to induce an apoptosis-like cell death. It is as far as possible to induce a specific antibody against original tumor cells, resulting from an application of this extreme specific and fragmented complex substance as an antigen. In addition, this antibody produced by antigenic substance inductor is applied as an antigen to produce a more highly sensitive and/or specific antibody.

Furthermore, a trial of tumor therapy has been performed by utilizing anti-tumor immune response. A substance to promote biological reaction against tumor is called as a biological response modifier. Such substances are bacterial-originated substances, fungal-originated substances, antibiotics and cytokines such as interleukin 2, interferon and tumor necrosing factor). Various examinations have been done. In addition, an antibody which is produced by utilizing idiotype antibody and/or anti-idiotyped antibody as antigen, which is also produced by antigenic substance inductor mentioned in this invention, is used to vital tissues obtained by endoscopic manipulation as well as surgical excision, removal and biopsy, utilizing with tissue culture. Thus, it is possible to induce a more specific anti-tumor effect depending on individual patient and/or various differences between oncogenic pathogenesis against several problems such as tissue specificity and tumor specificity of patients themselves. This possibility has been suggested by use of animals in same species. Tumor cells in an animal are killed by an adequate manipulation so that the killed cells are injected into another normal animal. When alived tumor cells are implanted in non-treated animal, the tumor cells grow and proliferate so that the animal was dead by tumor. However, an investigation shows that in the pretreated animal, tumor does not grow and is rejected. This fact is extremely similar to prevention of onset of infectious diseases by vaccination. However, an adequate method of killing cells with representative examples and reproducibility has not been presented. A fundamental logics in this invention is cooperatively identical to that mentioned in the international patent file (PTC: WO96/07403) related on inhibitory or blocking agents of molecular generating and/or inducing functions. This invention makes a disclosure of a biomedical logical process with representative examples such as anti-tumor and anti-neoplastic action. This invention can provide the antibody of which has a highly selective and specific vaccine, idiotype antibody and antibody produced by its idiotype antibody as an antigen. In addition, a designing of a specific activated immune response according to a request to prevent and/or treat diseases becomes to be possible. This issue has been expected. The following substances in this invention have been expected: vaccine precursor, vaccine, antibody, neutralizing antibody, antitoxin and idiotype antibody which is produced by use of antigenic substance inductor in this invention: and, vaccine, antibody, neutralizing antibody and antitoxin which is produced by its idiotype antibody.

Moreover, the following substances in this invention are able to control a molecular recognition of each receptor selectively and/or specifically: vaccine precursor, vaccine, antibody, neutralizing antibody, antitoxin and idiotype antibody of which is produced by antigenic substance inductor in this invention: and, vaccine, antibody, neutralizing antibody and antitoxin which is produced by its idiotype antibody.

A major significance of this invention is firstly demonstrated to obtain an antigenic substance which has a fundamental structure (conformation) determining its specificity dependent on species resulting from quantum thermodynamic changes in biological functions and/or blocking action of biological functions. These functions are generated and/or induced by multi-dimensional structure (topology and/or conformation) of macromolecules. Generation of functions and/or formation of a shape in biological and/or non-biological composites are dependent on multi-dimensional structures (conformation and/or topology) of its macromolecule.

As additional significance, this invention is demonstrated firstly to produce an antibody with a molecular recognition against substances with a high diversity in vivo. Moreover, industrial significance as well as medical significance demonstrated in this invention is also involved in the following: resolving unknown biological signal transmitting system and/or processing system of complex biological immune surveillance network such as cording, receiving and decoding.

Moreover, a major significance in this invention is to demonstrate that it is possible to inhibit and/or block biological cellular functions which are generated and/or induced by multi-dimensional structure (conformation). This specificity may be constituted to coexist and/or survive in environment, by an evolutional determinant factor of each species. In addition, there is a scientific significance to understand a mechanism of effects demonstrated in this invention by a theory of molecular orbital dynamics. Additionally, the practical significances are already mentioned in this invention. A social significance is to be able to fight against a treatment and/or prevention of intractable diseases as well as those efficiencies. Also, it is able to promote a beneficial utilization of substances with complex structure (conformation). For examples, it is sufficiently proposed to have an efficacy against a filterable pathogenic microorganism consisted of macromolecules, namely HIV infection which is a worldwide medical problem, together with biologically known scientific facts and examples demonstrated in this invention. Repeatedly again, a significance in this invention is that because this invention involves in a fundamental basis of logical returning toward a search of origin on scientific history as well as in a possibility of expectation of drug interaction, onset of side effects with combined drug uses and onset of drug resistant strain, and of those preventions.

Here, a fundamental principle of this invention is summarized. However, it is obvious that this invention is not limited by this mentioned summary. The purpose of this invention is to provide antibody with higher biological recognition and to produce and/or manufacture antitoxin and/or vaccine by use of a fragmented substance as an antigen, resulting from extinction of virus, rickettsia, bacteria and tumor cells. Those biological effects are utilized a destroying, extincting and/or fragmented action of a family of Yoshixol. These fragments become non-functional macromolecules of constituted components of cellular structure. In addition, a purpose of this invention is to produce a neutralizing antibody and antibody by utilizing action of which is able to alter stereo-chemical specificity of molecule thermodynamically and by utilizing a molecular mechanism of inhibitory or blocking agents of molecular generating and/or inducing functions. These points are suggested by the following effects of a family of Yoshixol which is a representative one of inhibitory or blocking agents of molecular generating and/or inducing functions. These effects is 1) that a family of Yoshixol is able to destroy cells (both of eukaryotes and prokaryotes) into granular particles with a size of 10-400 nm, 2) that there is a difference between morphological aspects of fragmented particles depending on species, 3) that a fragmented structure is easily deformed and solved by a heat accumulation of electron beam and is similar to morphological aspects of peptidoglycans and proteoglycans, 5) that such peptidoglycans and proteoglycans play an important role of mophogenesis of cells, are different between species and induce a species specificity, 5) such peptidoglycans and proteoglycans play an important role on cytokines, surface antibodies, generation of functions, structural formations and signal transduction (high affinity receptors), moreover 6) that such peptidoglycans and proteoglycans are major substances of extracellular matrix such as condroitin, fibrin and collagen, 7) that a family of Yoshixol is able to induce apoptosis, 8) a family of Yoshixol affects on methylation of G-proteins, a metylating stage, RNA-protein synthesizing stage of cells because of a fact that a flowcytometric analysis on cell cycle and action stage of a family of Yoshixol has suggested an arrest at Go/G1—early S phase, and 9) that a family of Yoshixol has a mechanism according to electron density and electron orbital (quantum theory) resulting in changes in multi-dimensional conformation of complex proteins such as enzymes (for examples, lipase, HIV protease and fanesyl transferase) and G-proteins which are known as signal interfaced substances so that a family of Yoshixol inhibits and/or control functional inductions.

Therefore, a family of Yoshixol is able to induce a fragmentation of morphological structure and to cease functions with a preserving process as far as possible of morphological elements and functions with a diversity of cells depending on DNA. Therefore, a substance (without heating and chemical manipulation) is obtained preserving a specificity of each cell. Animals of which are received such fragmented complex macromolecules as an antigen produce antibody themselves against the received complex macromolecular substance. Then, antibody becomes to be adequately and/or correctly recognize original cells resulting in removal of invasive non-self cells as foreign body. Thus, this mechanism is to selectively generate self-defense mechanism of antigen-antibody reaction and is to establish a new immune surveillance system. In order to understand proliferation, mitosis, transporting of substance and signal transduction between each cell and to utilize these scientific facts, however, it is needed to accumulate further scientific knowledge at the present. Thus, this invention is able to provide the following substances according to a stage of functional induction or at dynamic (for examples, chemical reaction, physical reaction and its interaction) activating stage of cells: vaccine precursor, vaccine, antibody, neutralizing antibody, antitoxin and idiotype antibody which is produced by use of combined substances as antigen: and vaccine, antibody, neutralizing antibody and antitoxin which is produced by its idiotype antibody.

Thus, a treatment with a family of Yoshixol is able to obtain an action of molecular recognition which induces super-selectiveness and/or specificity. Antibody followed by this invention is able to induce a higher selectiveness within diversity according to a biological self-recognition. In addition, it is possible to easily purify and condense a targeted molecule within complex macromolecules by utilizing an adequate vector, by a genetic cloning technology of cDNA from mRNA and by utilizing cell fusion technology. Furthermore, a molecular weight of Yoshixol used in this invention is extremely small so that it has a property of hapten and of direct actions on prion, virus, rickettsia, bacteria, bacterial toxin, tumor cells, various types of pathologic organs and tissues (namely, intractable diseases). In addition, a treatment with a family of Yoshixol promotes an additional activation of immune surveillance system in vivo when it is applied to obtain a direct action. Thus, it is easily thought with a reasonability to have a possibility of accumulating a synergistic therapeutic efficiency. It is obvious that when a family of Yoshixol (preventative dosage or less than lethal dosage) is given at an onset point of bacterial infections and/or tumor (cancer) in vivo, these constituted elements (granules and/or particles) of the fragmented cells become to stimulate immune system of the host and to produce an antibody, so that further proliferation and invasion in vivo as a circulus vitiosus is blocked by this positive feed-back mechanism.

Furthermore, obviously, it is possible to design and/or produce a specific neutralizing antibody and/or examination screening antibody against toxins resulting from a recognition of treated solution in vivo after in vitro preparation of a bacterial toxin. And also, obviously, it is possible that antibody against an artificial substance with complex macromolecule is produced in vivo. The produced antibody is isolated. This antibody has a property of a selective recognition against the artificial complex macromolecule. This application of producing antibody and/or molecular recognizing agent (for example, antibody catalyst) is required in industrial fields as well as in biological fields. It is possible to control a production of antibody molecule in the colloid (a liquid state of two substances without sedimentation).

In addition, it is obvious to analyze structure and determine molecular components of a targeted antibody from precipitin line of immuno-electrophoresis as demonstrated in examples of this invention, by utilizing conventional protein sequence analysis (western-blotting method and apparatus such as protein sequencer), liquid chromatography and mass spectrometer.

The invention claimed is:

1. A method of therapy of a cancer in an animal comprising treating cells of said cancer in vitro with a compound to extinguish the cells, collecting sediment of said treated cells and administering the sediment to said animal, wherein said compound has the Formula 3-a:

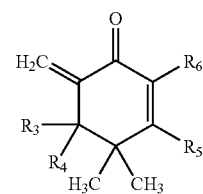

Formula 3-a wherein
R3, R4, R5 and R6 represent hydrogen atoms.

* * * * *